(12) United States Patent
Ubakar

(10) Patent No.: US 12,714,805 B2
(45) Date of Patent: Aug. 25, 2026

(54) BEVERAGE AND VAPOR DISPENSER

(71) Applicant: TAFÉE TECHNOLOGIES CORP., Toronto (CA)

(72) Inventor: Bruno Baker Ubakar, Toronto (CA)

(73) Assignee: TAFÉE TECHNOLOGIES CORP., Toronto (CA)

( * ) Notice: Subject to any disclaimer, the term of this patent is extended or adjusted under 35 U.S.C. 154(b) by 1104 days.

(21) Appl. No.: 16/622,994

(22) PCT Filed: Apr. 13, 2018

(86) PCT No.: PCT/CA2018/050450
§ 371 (c)(1),
(2) Date: Dec. 16, 2019

(87) PCT Pub. No.: WO2018/227275
PCT Pub. Date: Dec. 20, 2018

(65) Prior Publication Data

US 2020/0163375 A1 May 28, 2020

Related U.S. Application Data

(60) Provisional application No. 62/521,390, filed on Jun. 17, 2017.

(51) Int. Cl.
*A24F 40/465* (2020.01)
*A24F 3/00* (2006.01)
(Continued)

(52) U.S. Cl.
CPC ............ *A61M 11/042* (2014.02); *A24F 3/00* (2013.01); *A24F 40/00* (2020.01); *A24F 40/465* (2020.01);
(Continued)

(58) Field of Classification Search
CPC .... A24F 15/00; A24F 5/00; A24F 3/00; A24F 1/00; A24F 40/30; A24F 40/60;
(Continued)

(56) References Cited

U.S. PATENT DOCUMENTS 9,010,335 B1 * 4/2015 Scatterday ............ A61M 15/06 131/225
2013/0192623 A1 * 8/2013 Tucker ..................... H05B 3/16 131/329

(Continued)

OTHER PUBLICATIONS

Cambridge Dictionary, "synonyms". Pulled from website on Apr. 3, 2026 (Year: 2026).*

*Primary Examiner* — Alex B Efta
(74) *Attorney, Agent, or Firm* — Benesch Friedlander Coplan & Aronoff LLP

(57) ABSTRACT

The present invention is a beverage and vapor dispenser comprising a base unit as the lower portion of the invention whereupon a beverage container is mounted. The base unit incorporates a vaporizer that may function as a convection heater to produce vapor from a herb, oil, liquid or other substance. A conduit section extending along an interior or exterior side of the beverage container may engage with an outlet of the base unit, whereby vapor from the base unit may flow along the conduit section and be dispersed through the upper end of the conduit section. The conduit section may function in a similar manner to a straw or other conduit for the vapor. The beverage container may be filled with fluid and a person may drink the fluid from the beverage container simultaneously while the base unit is functioning to dispel vapor.

19 Claims, 26 Drawing Sheets

(51) Int. Cl.

| | |
|---|---|
| ***A24F 40/00*** | (2020.01) |
| ***A24F 40/20*** | (2020.01) |
| ***A24F 40/30*** | (2020.01) |
| ***A24F 40/42*** | (2020.01) |
| ***A24F 40/485*** | (2020.01) |
| ***A24F 40/57*** | (2020.01) |
| ***A24F 40/60*** | (2020.01) |
| ***A47G 19/22*** | (2006.01) |
| ***A61M 11/04*** | (2006.01) |

(52) U.S. Cl.

CPC ............ *A24F 40/485* (2020.01); *A24F 40/57* (2020.01); *A24F 40/60* (2020.01); *A47G 19/2227* (2013.01); *A24F 40/20* (2020.01); *A24F 40/30* (2020.01); *A24F 40/42* (2020.01); *A61M 2205/3368* (2013.01); *A61M 2205/3653* (2013.01); *A61M 2205/502* (2013.01); *A61M 2205/587* (2013.01)

(58) Field of Classification Search

CPC .......... A24F 40/57; A24F 40/20; A24F 40/10; A24F 40/00

See application file for complete search history.

(56) References Cited

U.S. PATENT DOCUMENTS

| | | | | |
|---|---|---|---|---|
| 2013/0239982 | A1* | 9/2013 | Meyer | A24F 13/12 131/328 |
| 2014/0060527 | A1* | 3/2014 | Liu | A24F 40/50 128/202.21 |
| 2015/0342259 | A1* | 12/2015 | Baker | A24F 40/485 131/329 |
| 2016/0366946 | A1* | 12/2016 | Murison | B67D 7/02 |
| 2017/0334606 | A1* | 11/2017 | Austin | A24F 9/14 |

* cited by examiner

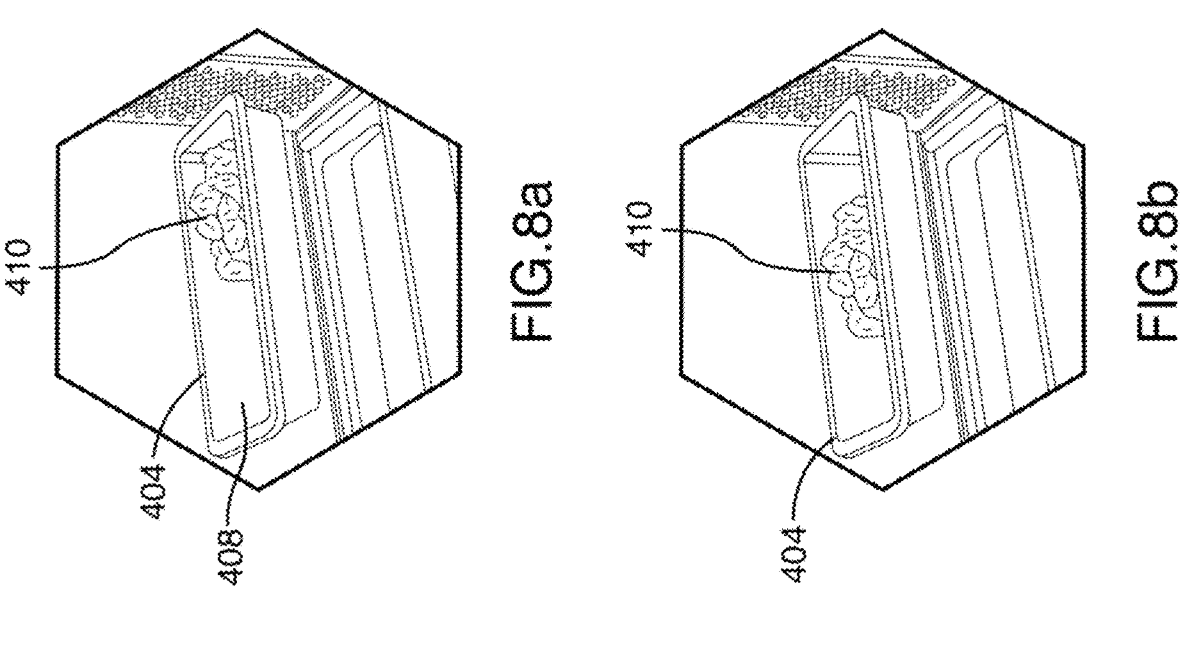
FIG.8a
FIG.8b
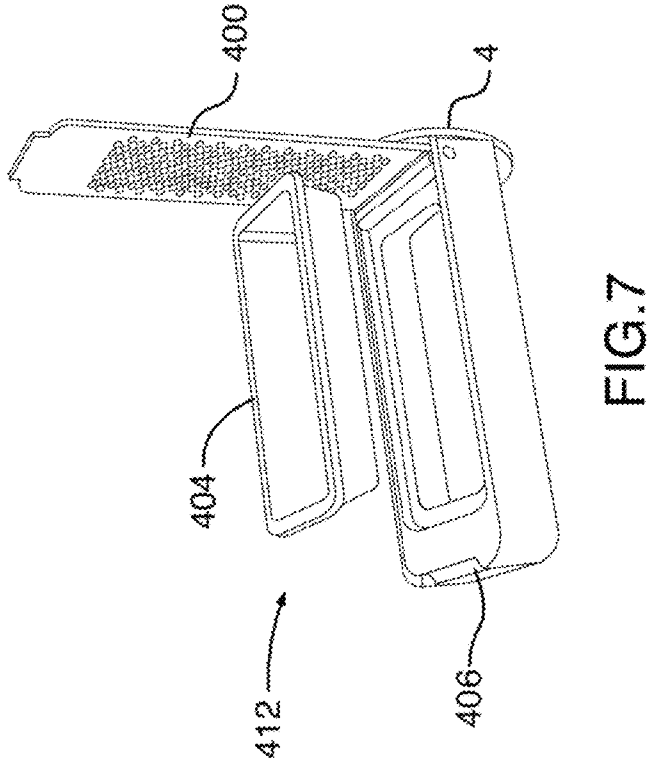
FIG.7

1024b
1024a
1022
12
10
20

1014
1010
1031
1012
1020
1008
1000

10
1034
30
1000
1022
20

1022
1024d
1024c
1024b
1024a
20
10
1028b
1026
1028a
30

10
1038
1052
30
1026
1028b
1028a
1050
20
1022
1024

200
230
290c
290d
290b
290a 30
1036
222
224
1034

200
262
30
230
20

20
240
242

20
242
240
244

242
20

242
20
240

BEVERAGE AND VAPOR DISPENSER

This application is a national stage application under 35 U.S.C. 371 of International Application No. PCT/CA2018/050450, filed Apr. 13, 2018, which in turn claims the benefit of U.S. Provisional Patent Application Ser. No. 62/521,390 filed Jun. 17, 2018, the contents of each of which are hereby incorporated by reference into the present disclosure.

FIELD OF INVENTION

This invention relates in general to the field of vaporizer units and more particularly to a beverage and vapor dispenser.

BACKGROUND OF THE INVENTION

Herbal vaporizer devices are used to vaporize active ingredients in plants, such as *cannabis*, tobacco, and other herbs. Such devices operate at a cooler temperature in comparison to the temperature required to smoke an herb from a pipe. The cooler temperature of a vaporizer unit is due to a lack of burning or combustion required for the device to function. Use of a vaporizer only requires that the herb be heated to the point at which the herb changes state from a solid to gaseous particles. This lack of burning or combustion in a vaporizer unit means that the herb is not destroyed by fire in the use of a vaporizer unit. An herb must be destroyed by burning or combustion in order to smoke the herb from a pipe. The result is that more efficient extraction of the active ingredients in such herb is possible through the use of a vaporizer, as compared to a smoking device that requires burning or combustion, such as a pipe.

Harmful effects experienced from smoking from a pipe, are reduced with the use of a vaporizer. Pipe smoke incorporates carbon monoxide, tar and other harmful toxins produced as a consequence of burning of the herb. The toxins produced by burning are not produced by a vaporizer and therefore are not inhaled by a user of a vaporizer.

Several forms of prior art vaporizer units are known including the following discussed herein.

U.S. Pat. No. 2,526,027 issued on Oct. 17, 1950 to A. J. Huck discloses a vaporizer unit for use with a medicament container that holds liquid medicament. The vaporizer functions such that the steam is generated from water within the vaporizer and the vaporizer is assembled such that the steam passes over the medicament so as to pick up the medicament vapors. The water is located in a lower section of the device in proximity to a heating element. The heating element functions to heat and vaporize the water. The medicament vapors are discharged from the vaporizer unit through a discharge spout. This prior art invention does not disclose use of the vaporizer units with herbs and requires water content.

U.S. Patent Application Publication No. 2012/0219274 filed on Feb. 28, 2011 by Mark Christopher Curran Jr. and Robert D. Schmid, and published on Aug. 30, 2012, discloses a UFO shaped vaporizer unit. The UFO vaporizer unit is powered by a power cord, and must be plugged into a wall socket to function. This prior art invention is not portable, or able to function with being plugged into a wall socket.

U.S. Patent Application Publication No. 20140053832 filed on Aug. 21, 2013 by Vaporfection International, Inc., and published on Feb. 27, 2014, discloses an herbal retention device for use with a vaporizing device. The herbal retention area is defined by a high-temperature resistant permeable herbal container body. A lower portion permits hot air to enter the herbal retention area, without allowing any herbal residue to exit. An upper portion defines a set of apertures sized to permit vapor to exit the herbal retention area, and a selectively openable aperture. This prior art herbal retention device incorporates a cap, that has the effect of allowing for an herb, or multiple herbs, to be transported and such retention device can be used in association with a vaporizer unit. Thus the prior art invention negates the need to store and transport herbs separately from a vaporizer unit and to insert the herbs into the vaporizer unit. Instead the vaporizer unit is used in association with the retention device. This invention is therefore used with a vaporizer unit, but does not disclose the integration of the retention device and the vaporizer unit.

SUMMARY OF THE INVENTION

In one aspect, the present disclosure relates to a beverage and vapor dispenser comprising: a base unit incorporating: a herb chamber operable to contain one or more herbs; a heating chamber operable to produce heat and generate vapor from a herb; and a vapor outlet, whereby the vapor can flow out of the base unit; a beverage dispenser removably connected to the base unit, said beverage dispenser being operable to contain and dispense liquid; and a conduit section having a hollow interior, said conduit section being removably connectable to the vapor outlet of the base unit and when so connected the vapor can flow from the base unit through the conduit section to a user.

In an embodiment of the present invention, the beverage and vapor dispenser may further comprise the heating chamber incorporating heating coils powered by a power source.

In an embodiment of the present invention, the beverage and vapor dispenser may further comprise the herb chamber having dry ice therein.

In an embodiment of the present invention, the beverage and vapor dispenser may further comprise a removable chamber tray incorporated in the herb chamber, wherein the herb is placed and from which herb residue is removed.

In an embodiment of the present invention, the beverage and vapor dispenser may further comprise a heat indicator in the base unit, said heat indicator being one of the following: one or more lights; or a screen operable to display information.

In an embodiment of the present invention, the beverage and vapor dispenser may further comprise a heat setting indicator in the base unit, said heat setting indicator being one of the following: one or more lights; or a screen operable to display information.

In an embodiment of the present invention, the beverage and vapor dispenser may further comprise a heat activation button operable to produce heat from the heating chamber.

In an embodiment of the present invention, the beverage and vapor dispenser may further comprise one or more of the following: a heat increase button; a heat decrease button; a heat setting increase button; and a heat setting decrease button.

In an embodiment of the present invention, the beverage and vapor dispenser may further comprise the base unit, conduit section and beverage dispenser being wholly detachable, whereby base unit, conduit section and beverage dispenser can be cleaned or repaired individually, or replaced before the beverage and vapor dispenser is reassembled.

In an embodiment of the present invention, the beverage and vapor dispenser may further comprise a tip removably attachable to an end of the conduit section that is not attached to the vapor outlet, said tip having a hollow interior.

In an embodiment of the present invention, the beverage and vapor dispenser may further comprise one or more holes in the tip, whereby vapor can flow from the tip when the tip is connected to the conduit section.

In an embodiment of the present invention, the beverage and vapor dispenser may further comprise said heating chamber being positioned above the herb chamber.

In an embodiment of the present invention, the beverage and vapor dispenser may further comprise an extension wall section attachable to or incorporated in the beverage dispenser, whereby the beverage dispenser is attachable to the base unit.

In an embodiment of the present invention, the beverage and vapor dispenser may further comprise a conduit section indentation in a wall of the beverage dispenser, wherein the conduit section is positioned virtually parallel to the wall of the beverage dispenser.

In an embodiment of the present invention, the beverage and vapor dispenser may further comprise a beverage dispenser incorporating a vapor viewable portion operable to contain and display vapor.

In an embodiment of the present invention, the beverage and vapor dispenser may further comprise the herb chamber incorporating multiple herb chambers or multiple herb cartridges.

In an embodiment of the present invention, the beverage and vapor dispenser may further be operable to generate the vapor by convection heating, said beverage and vapor dispenser comprising: the conduit section having the heating chamber incorporated therein; and the base unit incorporating an air inlet whereby air flows into the base unit, the conduit section being attachable to the base unit such that the heating chamber of the conduit section is positioned within the base unit in proximity to the heating chamber that is above the herb chamber, the heating chamber and air flow into the air inlet generating convection heating.

In another aspect, the present disclosure relates to a method of using a beverage and vapor dispenser, in accordance with the following steps: a. placing one or more herbs within an herb chamber in a base unit of the beverage and vapor dispenser; pouring liquid into the beverage dispenser of the beverage and vapor dispenser; activating a heating chamber to produce heat, whereby vapor is generated from the herb; a user inhaling vapor flowing from the base unit through a conduit section; and dispensing the liquid from the beverage dispenser to the user.

In an embodiment of the present invention, the method may further comprise the step of the user inhaling vapor from the conduit section by mouth, by sucking on the conduit section.

In yet another aspect, the present disclosure relates to a beverage and vapor dispenser comprising: two or more beverage dispensers each incorporating a hollow vapor holding section having a vapor inlet and a vapor outlet therein, and a vapor conduit section being hollow and removably connectable to the vapor outlet; a hollow vapor tray incorporating a vapor tray inlet, and two or more vapor dispensers having a door therein that is openable when the vapor inlet of a beverage dispenser is positioned upon the vapor dispenser; a vaporizer base unit incorporating a heating chamber operable to produce heat and generate vapor from a herb within a herb chamber, and a vaporizer outlet; and a hollow connector having a first end connected to the vapor tray inlet and a second end connected to the vaporizer outlet; whereby the vapor flows: from the vaporizer base unit through the connector into the vapor tray; from the vapor tray through a vapor dispenser into the vapor holding section of a beverage dispenser placed thereupon; and from the vapor holding section through the vapor conduit section to a user.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The invention will be better understood and objects of the invention will become apparent when consideration is given to the following detailed description thereof. Such description makes reference to the annexed drawings wherein:

FIG. 7 is an exploded view of the elements of the herb chamber of the beverage and vapor dispenser, of an embodiment of the present invention.

FIG. 8*a* is an upper-side view of the chamber tray element of the herb chamber of the beverage and vapor dispenser, of an embodiment of the present invention, having dry ice and herb therein.

FIG. 8*b* is an upper-side view of the chamber tray element of the herb chamber of the beverage and vapor dispenser, of an embodiment of the present invention, having an herb therein.

Figure 2:
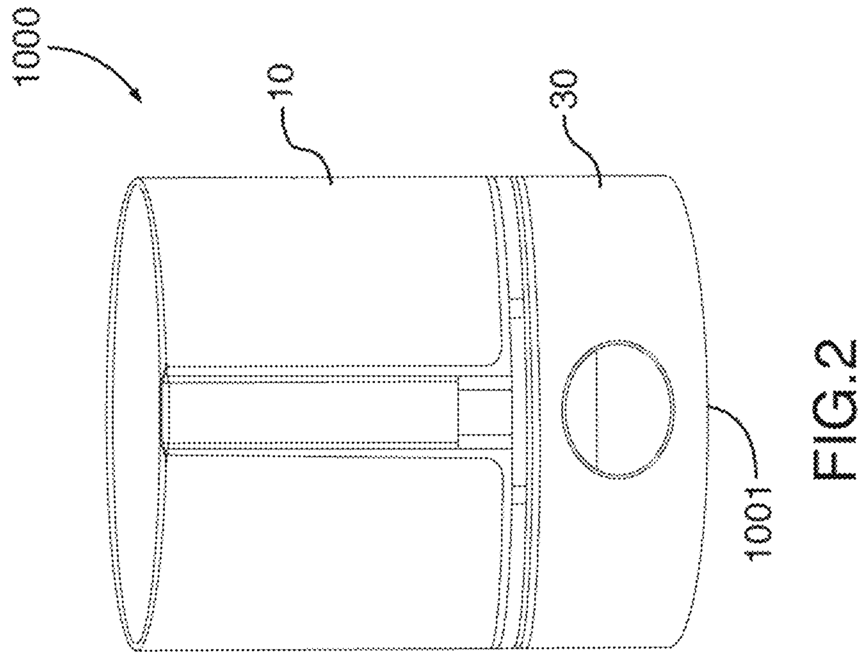
FIG. 2 is a rear perspective view of the beverage and vapor dispenser, of an embodiment of the present invention.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE PREFERRED EMBODIMENT

The present invention is a beverage and vapor dispenser comprising a base unit as the lower portion of the invention whereupon a beverage container is mounted or otherwise removably attached. The base unit incorporates a vaporizer that may function as a convection heater to produce vapor from an herb, oil, liquid or other substance. A conduit section extending along an interior or exterior side wall of the beverage container may engage with an outlet of the base unit, whereby vapor from the base unit may flow along the conduit section and be dispersed through the upper end of the conduit section. The conduit section may function in a similar manner to a straw or other conduit for providing the vapor to a user. The beverage container may be filled with fluid and a person may drink the fluid from the beverage container simultaneously while the base unit is functioning to expel vapor.

The conduit section may be of any shape, such as round, rectangular, octagonal, or any other shape, having a hollow interior wherein vapor may flow through the conduit section. The conduit section of the present invention may be removably attached to an outlet formed in the base unit, or to an outlet tube that connects the conduit section to the outlet. The outlet may incorporate a silicone gasket that is used to attach the conduit section to the outlet in the base unit in some embodiments of the present invention of the present invention. The removal of the conduit section allows for the conduit section to be cleaned separately from the other elements of the present invention.

In some embodiments of the present invention, the conduit section may have an herb chamber incorporated therein that is operable to hold a chamber tray. The housing chamber may be cleaned with the conduit section, whereas the chamber tray may be cleaned separately from the conduit section. This allows for vapor residue and herb, oil, liquid or other substance residue to be removed from the conduit section, herb chamber and chamber tray.

Other elements of the present invention may also be detached from the invention, for cleaning or other purposes. For example, the beverage container may be detached to be cleaned separately from the other elements of the present invention. Other detachable elements of the invention are described below, including a chamber tray, a tip for the conduit section, etc.

The present invention may have two distinct uses. The base unit may be used as a vaporizer and the conduit section may be used to transfer vapor from the base unit to a user. The base unit elements of the present invention may be utilized to vaporize any type of herb, for example, such as basil, chamomile, damiana, *eucalyptus*, green tea, hops, lavender, peppermint, rosemary, thyme, *cannabis*, tobacco, or other types of herbs, substances, oils or liquid that can be vaporized using a vaporizer. The vaporizer may be utilized for aromatherapy purposes, medical or therapeutic purposes, recreational purposes, or other purposes achieved by vaporizers, depending on the herbal, substance, oil or liquid with which the vaporizer is utilized.

For example, the vaporizer may be utilized with lavender, in herb or oil form, for aromatherapy purposes, whereby a user will breathe in vapors by nose or mouth that induce a calming effect upon the user. As another example, the vaporizer may be utilized with an herb such as *eucalyptus*, whereby a user will breathe in *eucalyptus* vapors by nose that help alleviate congestion symptoms of a user. As yet another example, the vaporizer may be utilized with an herb such as *cannabis* that is prescribed by a medical professional for medicinal uses in relation to an illness or disease, and the user may inhale vapors by mouth that help treat such illness or disease or have therapeutic effects relating to such illness or disease. As yet another example, the vaporizer may be utilized with an herb such as tobacco for recreational purposes, whereby a user will breathe in vapors by mouth. A skilled reader will recognize that other herbs, oils, liquids and other substances may be utilized with the vaporizer by a user for other aromatherapy purposes, medical or therapeutic purposes, recreational purposes, or other purposes.

For clarity, any reference herein to any "herb" that can be vaporized in the base unit, may be read to reference an herb, oil, liquid or other substance.

The beverage container may be used as a means of storing and dispensing beverages, in the manner of a pitcher or a cup. The beverages may hot or cold beverages of any nature, for example, such as coffee, tea, milk, juices, alcoholic beverages, water, or any other type of liquid. A user may drink liquids from the beverage dispenser, or the beverage dispenser may have a lid attachable thereto, and may be used to transport beverages.

The present invention may have design elements whereby it is perceived by a viewer as a stylized beverage dispenser, similar to a travel mug, a flask, or a portable cup. In this manner the integration of the vaporizer unit in the present invention may be concealed or camouflaged from a viewer. Embodiments of the present invention may be configured to be stylized, for example, such as designed in a particular shape, or to display particular brands, or in particular colours, coatings or other finishes. Other embodiments of the present invention may be designed to exude a particular aesthetic, for example, such as a sleek exterior, a compact configuration, an elegant appearance, a patterned exterior, a molded shape whereby the invention appears to be a form of artwork, or any other aesthetic. Embodiments of the present invention may be formed of a variety of materials for such aesthetic purposes, such as wood, precious metals and alloys, stones and fabricated finishes.

Embodiments of the present invention may incorporate a vapor section that extends along the whole or a portion of the side of the beverage dispenser. In such embodiments, the beverage dispenser fits wholly or partially within the vapor section. The vapor section may further have transparent outerwalls, such that vapor present within the vapor section may be visible.

In embodiments of the present invention, the vaporizer function that occurs in the base unit may be achieved through use of convection heating, which allows for vapor to be generated from an herb at a cooler temperature than is achieved by prior art inventions. Embodiments of the present invention may further incorporate cooling features in the configuration of elements of the invention, such as the base unit and/or the conduit section, or cooling elements to be placed in the invention, such as dry ice, to cause the vapor inhaled by the user to be at a cooler temperature than is achieved by prior art inventions. In embodiments of the present invention, the vaporizer may be configured such that the heating coils are positioned above the herbs, and the heating chamber and chamber tray that contains the herbs may be wholly or partially enclosed within a section of the base unit that is separated by a wall from other parts of the base unit, for purpose of focusing all of the heat generated by the heating coils upon the herbs, and to avoid heat loss due to heat escaping to other areas of the base unit. These aspects of the present invention can have benefits for the taste and smoothness of the vapor as experienced by a user who inhales the vapor by mouth or nose.

The present invention has several advantages over the prior art. The vaporizer integrated within the base unit may incorporate elements, configurations and/or dry ice whereby the temperature of the vapor may be cooled before it is inhaled by a user. Although there can be health benefits to inhaling a warm moist vapor, the same benefits are not experienced from inhaling a warm dry vapor. Therefore, cooling of the vapor prior to a user inhaling said vapor can have benefits for a user. Furthermore, the cooling of the vapor enhances flavor of the vapor and the smoothness of the vapor as experienced by the user who inhales the vapor by nose or by mouth. Embodiments of the invention can further incorporate dry ice in the herb dispenser, or in other elements of the invention, such as in the conduit section, which can allow for flavors of the herb to be retained and possibly amplified at the time of inhalation by a user.

Embodiments of the present invention may further incorporate a vapor director, whereby the amount of vapor that is dispersed from the vaporizer and the base unit generally, and that is available to a user to inhale in a single inhalation, may be measured. This element of the present invention may be of benefit to particular users who fare better if they can inhale a limited amount of vapor at a time. A vapor director may constitute a tip for a conduit section, or other configurations or elements of embodiments of the present invention.

The present invention further has the benefit of being convenient, in that a user can transport a single object that offers two functions, beverage dispenser and vapor dispenser. A user of a vaporizer is often thirsty after using the vaporizer, and therefore the present invention is convenient for a user. It provides a means whereby the user can drink immediately after using the vaporizer. The present invention further offers a discrete manner of transporting a vaporizer unit in that it is integrated with a beverage dispenser, and the invention has the appearance of a beverage dispenser.

The base unit of the present invention additionally overcomes disadvantages of the prior art in that it provides a vaporizer integrated with an item that people commonly utilize or transport with them, namely a cup, mug, beverage bottle, or other beverage dispenser. By integrating a vaporizer with a commonly transported item, a person is not required to transport two items separately in order to have a beverage dispenser and a vaporizer on hand. Instead a person can reach for, and only have to transport, one item, a beverage dispenser having a vaporizer integrated therein, in order to have the functionality of both items at hand.

The present invention further can be configured to be aesthetically pleasing, which differs from the prior art that is generally merely functional, rather than aesthetically pleasing. The present invention may further differ from the prior art in that it may have visual similarities to a beverage dispenser, and the vaporizer unit of the present invention may be essentially camouflaged. This has the benefit that any stigma that may be attached to use of a vaporizer, for example, such as stigma attached to smoking that may occur if the vaporizer is used by a user with tobacco, may be avoided by the user if the user is seen carrying or otherwise displaying the present invention. The invention can therefore assist users of vaporizers to discretely carry their vaporizer without drawing undue attention to said vaporizer.

The present invention may further overcome disadvantages of the prior art in that its heat and vapor path may be configured to efficiently vaporize the herbs at a relatively cool temperature and to cool the vapor before it is inhaled by nose or mouth by a user. The present invention may also be configured to efficiently vaporize the herbs while maintaining a relatively cool ambient temperature in the base unit, and to significantly cool the vapor before it inhaled by nose or more mouth by a user. The heat and vapor path of the present invention include the heating chamber and the conduit section. In embodiments of the present invention the heating chamber may be raised and suspended above the herb chamber. The effect of the cooler temperature at the point of generating the vapors, and of the vapors generally as may occur in or near the herb chamber and/or the conduit section (as compared to the temperatures at the same stage as undertaken by the prior art), is that the flavors of the herbs, oils, liquids or other substances from which the vapor is produced will be amplified for the user inhaling the vapor by nose or mouth. Specifically, the inverted pull of air through the conduit section (as created by the user sucking upon the conduit section) can create a convection heating effect as it causes air to pass over the heater coils in the vaporizer unit, through the contents of the herb chamber, and through the conduit section. The conduit section may be formed of materials that conduct heat well. This can cause the vapor to be generated and/or inhaled at a cooler temperature than occurs in the prior art. Additionally, the conduit section and/or the herb chamber may be configured to contain dry ice (C02). The dry ice sublimates from solid to gaseous form (C02) and bonds with the vapor generated from the herb, oil, liquid or other substance, to create a carbonated taste for a user who inhales the vapor from the conduit section by nose or mouth.

The present invention further offers benefits over the prior art in that embodiments of the present invention are configured such that multiple herbs may be loaded into separate compartments of the base unit of the present invention. The base unit may be operable to produce vapor from one of the herbs in a particular compartment, or multiple herbs in multiple compartments. The base unit may further be configured such that the one or more cartridges that vapor will be produced from may be selectable by a user. In this manner the invention may be utilized to produce vapor from several different types of herbs, and the different types of herbs may be transported within the base unit.

Embodiments of the present invention offer the further benefit of permitting the most up to date vaporizer technology and beverage dispenser aesthetics or functions to be integrated in the invention. The base unit wherein the vaporizer is incorporated is removeable from the beverage dispenser, and may be updated to offer the newest vaporizer technology. In a like manner the beverage dispenser that is attached to the base unit can be changed, such as to incorporate a beverage dispenser with specific functionalities or aesthetics. The functionality and aesthetics of the present invention can thereby be adapted and modified overtime.

Figure 1:
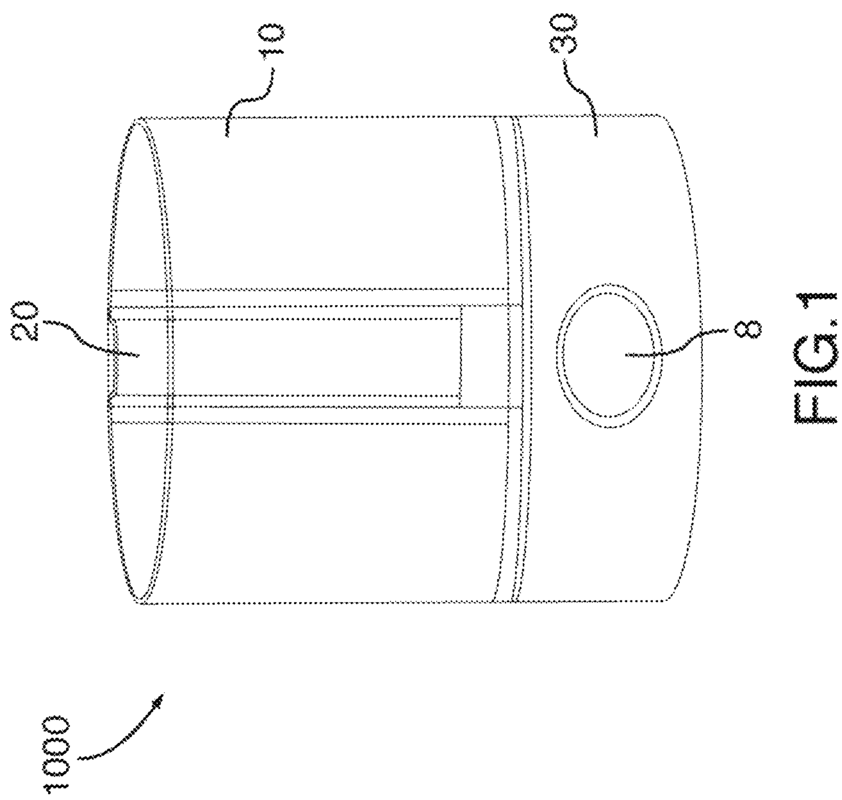
FIG. 1 is a front perspective view of the beverage and vapor dispenser, of an embodiment of the present invention.

As shown in FIG. 1, a vapor dispenser comprises a beverage dispenser 10 attached to a base unit 30. The base unit incorporates elements that function as a vaporizer unit, as described herein. The vaporizer unit is operable to generate vapor that incorporates the essence of an herb or some other substance. The invention further incorporate a conduit section that extends from an outlet in the base unit, such that vapor from the base unit can flow along the conduit section, and thereby be delivered to the user. The conduit section may be similar in structure and function to a straw.

Figure 30:
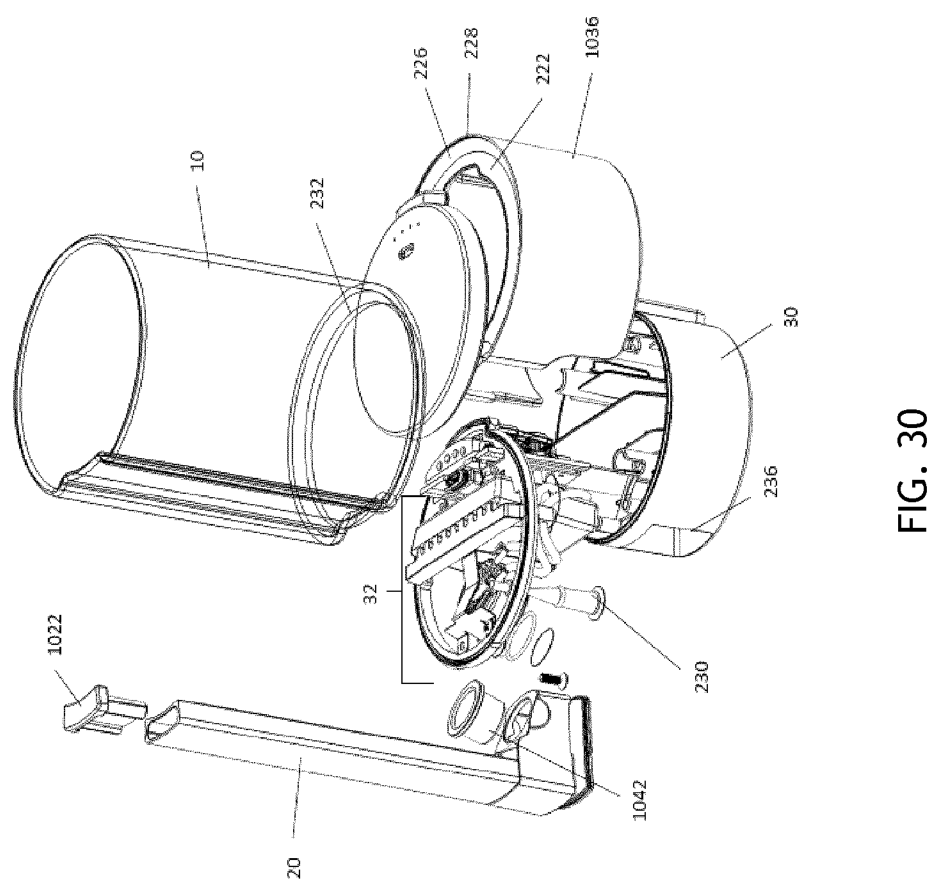
FIG. 30 is an exploded of a beverage dispenser, base unit without a base unit housing, conduit section and chamber tray, of an embodiment of the present invention.

The beverage dispenser may be formed of any material operable to hold liquids, such as glass, plastic, metal, ceramic, or any other material. The beverage dispenser may also be operable to dispense any liquid housed therein directly to a user drinking therefrom. Another operability of embodiments of the beverage dispenser may be to pour liquid therefrom into another vessel, such as a glass or other container. The liquid may be a beverage or another type of liquid that the beverage dispenser is operable to contain. The liquid may be hot or cold. As shown in FIG. 30, the beverage dispenser may be insulated or made of a material having insulating properties, such as ceramic, if it is to be utilized to house hot liquids.

The beverage dispenser either incorporates or is aligned or virtually aligned with a conduit section 20. The conduit section is connected to an outlet in the base unit, whereby vapor or other gases can flow from the base unit into the conduit section. The base unit housing may be formed of any material able to maintain its shape when heated, such as certain plastics, silicone, glass, metal, aluminum, steel, ceramic, steatite, or any other material suitable for the purpose. The contents of the base unit are described herein.

The conduit section is elongated so that it is extends the whole, virtually the whole, or beyond of the length of side of the beverage dispenser. The conduit section may be shaped to have a circular circumference, or be of any other shape, whether that shape is regular and consistent or a changing shape along the elongated edges of the conduit section. The base unit may incorporate a heat activation button 8 or other mechanism operable to activate the heating elements within the base unit.

As shown in FIG. 2, the base unit may incorporate a door or release mechanism 1001 whereby access to the herb container may be achieved. When the herb container is accessed herbal content, such as an herb, can be inserted into the herb container. The herb container, or herbal chamber, can then be reinserted into the interior of the base unit. When the heat activation button is utilized the heater will be caused to function, such that the herbal content of the herb container is heated and vapors are generated from the herbal content. The vapors can escape the base unit through the outlet that is attached to the conduit section of the beverage dispenser. A user can use the conduit section in the manner of a straw to suck or otherwise inhale vapors into their mouths and thereby into their air passage or lungs. Alternatively a user may inhale the vapors from the conduit section via other methods, such as via their nose at a close proximity or a distance from where the vapor is expelled from the conduit section.

The conduit section may be of varying widths and lengths, and thereby be configured to be operable to hold a particular maximum volume of vapor. The narrower the width of the conduit section the more concentrated the vapors inhaled by the user, by mouth or nose, may be, and therefore the width of the conduit section may be specifically configured for use by particular users who require a more or less concentrated vapors to be provided to be inhaled by such user. The conduit section may further be of varying widths along the length of the conduit section. The longer the conduit section the cooler the vapor may be before it is inhaled by a user, which can have benefits, as discussed herein.

Figure 3:
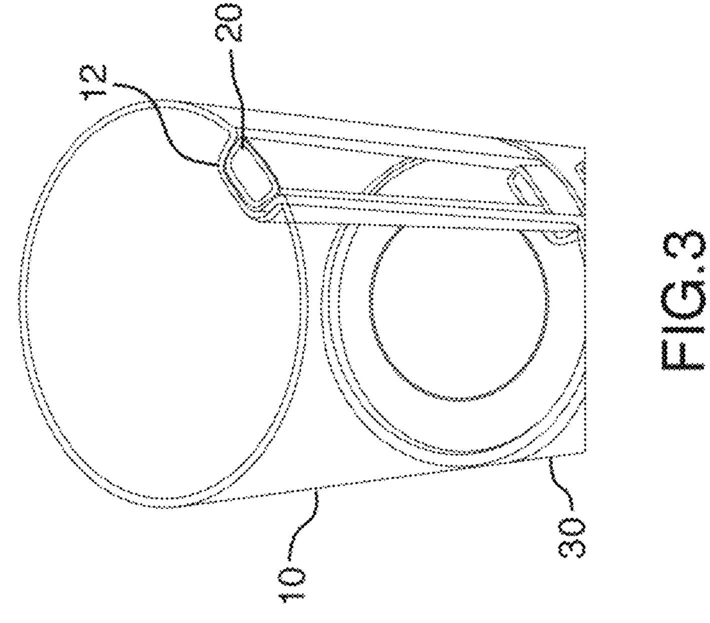
FIG. 3 is a perspective view of the beverage and vapor dispenser, of an embodiment of the present invention.

As shown in FIG. 3, the beverage dispenser 10 may be configured to incorporate a conduit indentation 12 that is shaped so that the whole or a portion of the conduit section 20 may fit within such conduit indentation. In one configuration of the present invention the conduit section is outside of the beverage dispenser, but positioned to be parallel or virtually parallel to the beverage dispenser. The conduit section 20 may be attachable to the beverage dispenser by an attachment mechanism built into the conduit indentation. Alternatively, the conduit section may not be attached to the beverage dispenser. The conduit section may be detachable, or consistently detached from the beverage dispenser, such that when the conduit section is detached from the outlet of the base unit, the conduit section may be cleaned and/or stored separately from the beverage dispenser and the base unit.

Figure 4:
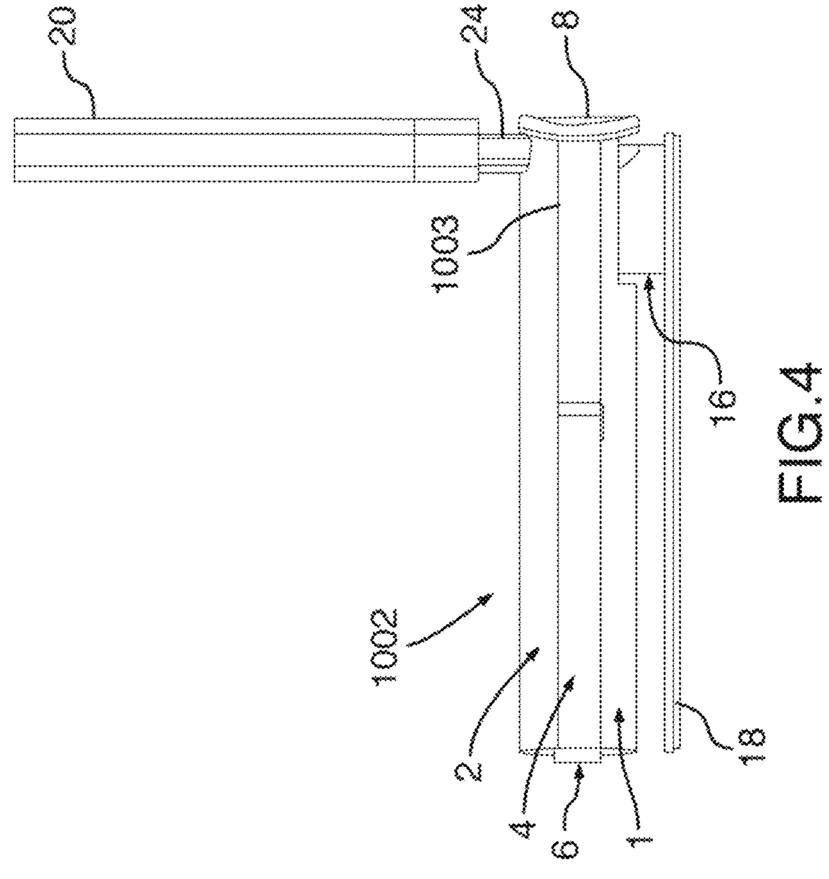
FIG. 4 is a side perspective view of the elements of vaporizer unit of the beverage and vapor dispenser, of an embodiment of the present invention.

In some embodiments of the present invention, the conduit section may be attached to the outlet formed in the housing of the base unit or a portion of the conduit section may be inserted directly within the base unit. In other embodiments of the present invention the conduit section 20 may be fit over an outlet tube 24 extending from a manifold outlet 1003 attached to the manifold 1002, as shown in FIG. 4. The outlet tube may be formed of a variety of materials, such as plastic, metal, silicone, or any other material suitable for the purpose. The manifold is positioned within the housing of the base unit, and the heating chamber and base may also be positioned within the housing of the base unit. In some embodiments of the present invention, a portion of the manifold outlet may extend externally from the housing of the base unit.

The manifold 1002 incorporates an upper manifold 2 and a lower manifold 1. An herb chamber 4 is positioned between the upper manifold and the lower manifold. An access door 6 is positioned on the end of the herb chamber that is opposite from the heat activation button 8. The access door may incorporate a handle, whereby the door may be opened. The access door may be connected to the upper manifold or lower manifold or some other portion of the manifold by one or more hinges and may swing open when the handle is pulled. Alternatively the access door may be releasable in some other manner, for example, such as releasable upon force exerted upon the access door, whereby when the access door is pushed upon on its external side, the access door may react by moving into an open position. The access door may also be openable by other means. Once the access door is opened a user will have access to the herb chamber, whereby content, such as an herb, can be added to or removed from the herb chamber. In some embodiments of the present invention, the herb chamber may be removed from the base unit when the access door is open. The access door will be closeable after it has been opened by an exertion of force upon the access door to move the access door from an open position to a closed position.

The heating chamber is positioned upon a base section 18. In some embodiments of the present invention, the heating chamber is positioned below the lower manifold at the end of the lower manifold that is closest to the heat activation button 8. The heating chamber may be a ceramic heating chamber, or another type of heating chamber.

In one embodiment of the present application a 1,200 mAh battery may be incorporated in the base unit and connected to the heating chamber, to power the heating chamber. Alternatively, other batteries or power sources may be utilized or designed to provide power to the heating chamber. The battery or other power source of the base unit may further be attached to any lights or screens in the base unit, or other elements in the base unit requiring power.

The heat activation button 8 is operable to cause the heating chamber to generate heat. The heating chamber is connected to the heat activation button, whereby force exerted upon the heat activation button will cause the heating chamber to start to heat up. In some embodiments of the present invention, the heating chamber will only generate heat while the activation button is depressed, or otherwise activated by a user. In other embodiments of the present invention, when the heat activation button is pressed the heating chamber will begin to heat and will stop heating after a period of time, or once a specific temperature is generated and sensed by a heat sensor located within the heating chamber.

The heat generated by the heating chamber will heat the content of the herb chamber, which may be any type of herb, oil, liquid or substance, as described herein. A user can insert any type of content into the herb chamber, such as one or more herbs, or combinations of two or more, or two or more types, or any of the following: herbs, oils, liquids, or other substances.

Once the content of the herb chamber is heated it may produce vapors. In an embodiment of the present invention, the upper manifold may have a hollow interior. The vapors will be dispersed from the herb chamber into the hollow interior of the upper manifold. The vapors will collect in the upper manifold and be released from the upper manifold when the manifold outlet is open. The manifold outlet is aligned with the outlet of the base unit. As described herein, the conduit section may be connected directly to the aligned manifold outlet and outlet of the base unit, or an outlet tube may be connected to the aligned manifold outlet, so that when the manifold outlet is opened vapors will move from the upper manifold into the outlet tube. The outlet tube will extend through the outlet of the base unit that is aligned with the manifold outlet. The outlet tube may extend externally from the housing of the base unit. The conduit section may either be fit over, or within the outlet tube, so that the conduit section forms a continuation of the outlet tube, and vapors can travel from the outlet tube to the conduit section.

The volume capacity of the hollow interior of the upper manifold may vary in embodiments of the present invention. The upper manifold may thereby be configured to be operable to hold a particular maximum volume of vapor. The configuration of the upper manifold may affect the rate and volume at which vapors move from the upper manifold into the conduit section. The upper manifold may be specifically configured for use by particular vapor delivery requirements of users.

In some embodiments of the present invention the conduit section may have a stopper that can be fit within an end of the conduit section, and thereby block vapors or any gas from escaping from the conduit section. In some embodiments of the present invention the outlet of the base unit may have a base unit outlet stopper that can be fit within the outlet of the base unit. When the base unit outlet stopper is fit within the outlet of the base unit vapors or other gases in the base unit, or any element within the base unit, such as the manifold, may be prevented from escaping the base unit.

Figures 5, 6:
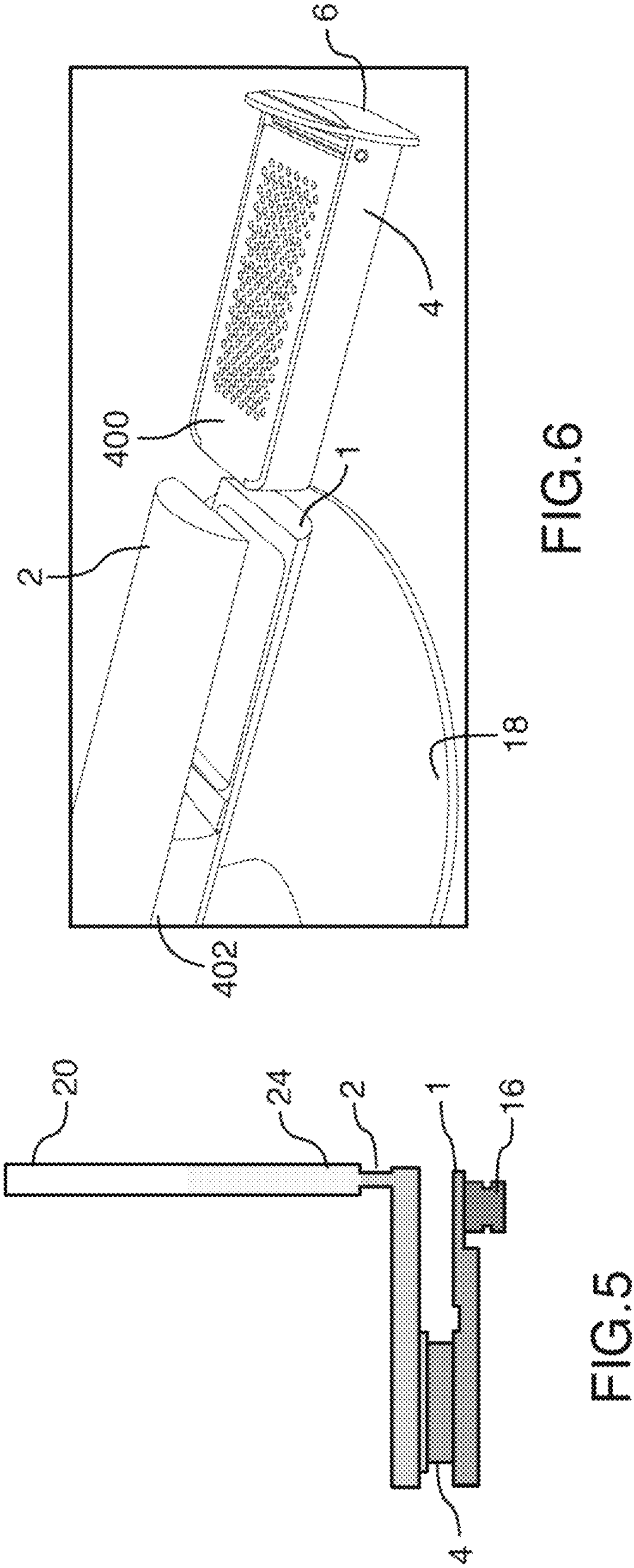
FIG. 5 is a side perspective view of the elements of vaporizer unit of the beverage and vapor dispenser indicating a range of thermal temperatures therewithin, of an embodiment of the present invention.
FIG. 6 is an upper-side perspective view of the herb chamber of the beverage and vapor dispenser, of an embodiment of the present invention.

As shown in FIG. 5, the degree and intensity of heat experienced by portions and elements of the present invention may vary when the heating chamber is activated. The highest degree of heat is indicated by darker shading and the lowest degree of heat is indicated by shading. Gradients of shading between the darkest shading and no shading indicate varying levels of degrees of heat in FIG. 5.

The base unit of the present invention may be configured to function to cool the vapor, as shown in FIG. 5. The result of this function of the present invention is that a user may inhale a cooler more pleasant vapor through the conduit section.

As shown in FIG. 6, the herb chamber 4 may be removable from the manifold. The herb chamber may incorporate a lid 400 having one or more holes therein. The lid and herb chamber may be formed of plastic, glass, metal, silicone, stainless steel or any other material operable to keep its shape and withstand heat, and otherwise serve the purpose of such element in the invention. The vapors generated by heating the content of the herb chamber may be released from the herb chamber through said holes in the lid. As shown in FIG. 7, the lid 400 may be moveable such that it can be removed from blocking access to the chamber tray 404. For example, the lid may be connected to the herb chamber by one or more hinges, and may be rotated in accordance with the function of the hinge, from a closed to an open position and from an open to a closed position. The lid may also snap closed over the herb chamber to secure the chamber tray in place. The lid may further be fully removable from the herb chamber, or otherwise wholly or partially removable from the herb chamber.

The herb chamber may be held in place by at least one magnet that may be disposed beneath the herb chamber.

The chamber tray may be wholly removable from the herb chamber. When removed from the herb chamber, the chamber tray can be emptied of content, or content can be inserted within the chamber tray. The tray can further be cleaned when it is removed from the herb chamber. The chamber tray can be reinserted into the herb chamber after it is removed from the herb chamber.

The content of the herb chamber is positioned directly within the chamber tray. The chamber tray may be formed of a solid or perforated material. A chamber tray that is formed of a material that is perforated may incorporate one or more holes. For example, the chamber tray may be formed of a mesh material. A chamber tray may also be formed from a porous material. A chamber tray that is formed of a perforated material may be operable so that vapors generated from heating the content of the herb chamber may move from the chamber tray, through the holes therein, into the base unit lower manifold and/or otherwise within the base unit housing. The number of perforations, and/or the degree of porousness of the material from which the chamber tray is formed will affect the volume of vapor that escapes from the chamber tray simultaneously and the rate of the escape of the vapor from the chamber tray. For example, if the chamber tray is formed of a mesh material or a highly porous material, the volume of vapor that will escape from the chamber tray simultaneously will be higher than experienced if the chamber tray was formed of a less perforated, solid or less porous material. Likewise, if the chamber tray is formed of a mesh material or a highly porous material, the rate of escape of vapor from the chamber tray will be higher than experienced if the chamber was formed of a less perforated, solid or less porous material.

The material that the chamber tray is formed of may vary in embodiments of the present invention, and will affect wherein the base unit housing and the manifold that vapors are directed, as well as the rate and simultaneous volume of the release of vapors from the chamber tray.

The material that the chamber tray is formed of will also affect how quickly the content of the chamber tray is heated. For example, the heat conductibility of the material, the porousness and/or number of perforations of the material that the chamber tray is formed of will all affect how quickly and efficiently the heat from the heating chamber heats the contents of the chamber tray. For example, a more porous material, a more perforated material and a material that conducts heat well, may cause the content of the chamber tray to be heated more quickly by the heat from the heating chamber than a chamber tray that is formed of a less porous material, a material that is solid or incorporates few perforations and/or a material that is a poor conductor of heat.

As shown in FIG. 8*a*, combinations of content may be positioned within the chamber tray 404, such as herbs 410 and dry ice may assist in providing vapor at a cooler temperature when in-use, as described herein. The combinations of content inserted in the chamber tray may further be multiple herbs, herbs and medications, or any other combinations of content. As shown in FIG. 8*b*, the content of the chamber tray may further be a single herb 410, or any other uniform type of content.

Figures 9, 10:
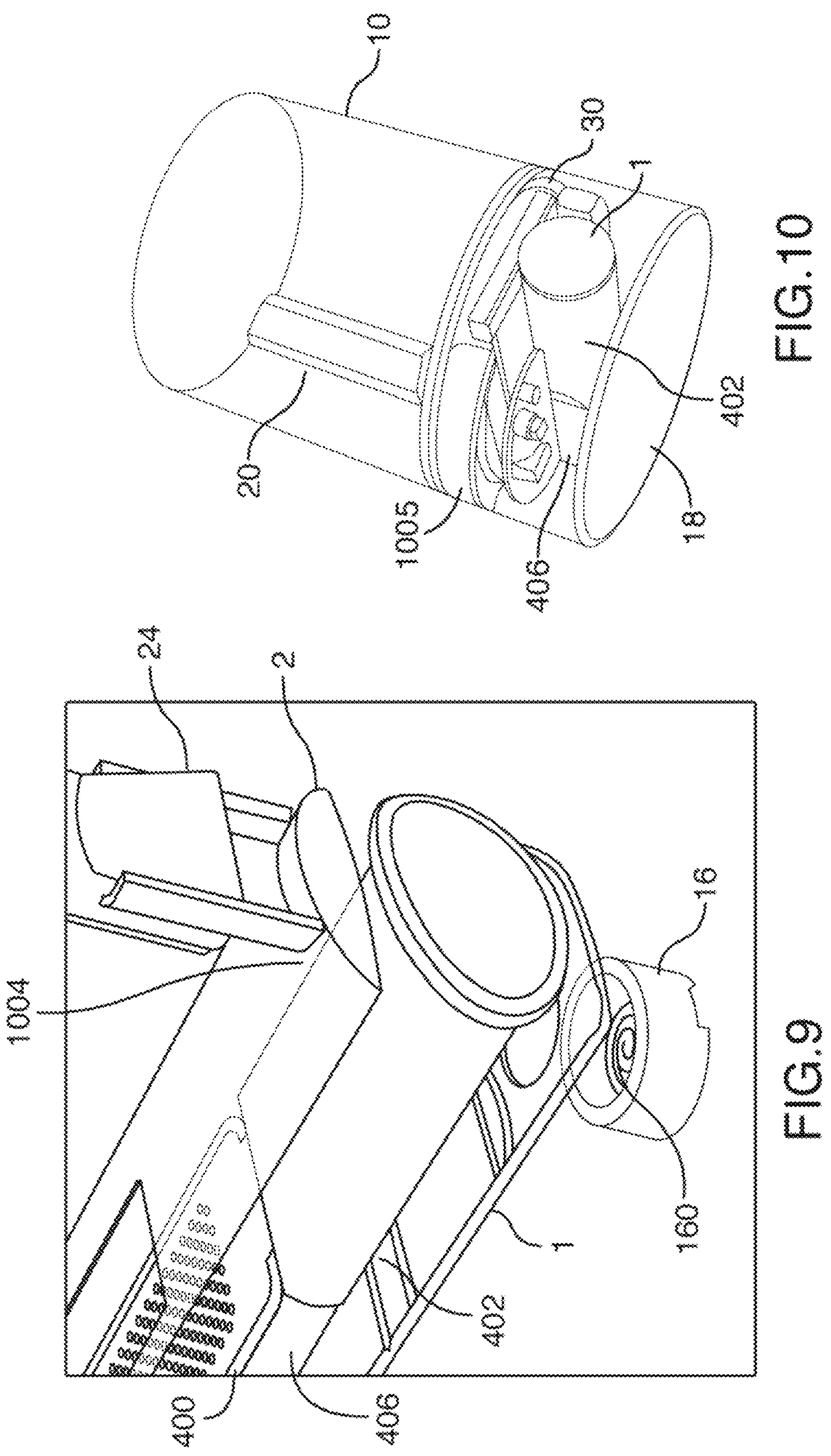
FIG. 9 is a back perspective view of the heating chamber aligned with other elements of the vaporizer unit of the beverage and vapor dispenser, of an embodiment of the present invention.
FIG. 10 is a back perspective view of the beverage and vapor dispenser, of an embodiment of the present invention, wherein the vaporizer unit housing is formed of transparent material.

As shown in FIG. 9, the heat activation button may be connected to a heat transfer element 402 adjacent to the herb chamber. The heat transfer element may be formed of a heat conductive material, and as the heating chamber 16 releases heat, the heat conductive material of the heat transfer element transfers heat to the herb chamber, and thereby heats the herb chamber and the contents of the chamber tray.

In some embodiments of the present invention, the upper manifold 2 and lower manifold 1 may be formed to have edges and sides that do not contact any portion of the heat transfer chamber and that do not form any hollow interior within either the upper manifold or the lower manifold. The portion of the lower manifold positioned direction above the heating chamber may incorporate a hole whereby heat may pass from the heating chamber directly to the heat transfer element. The heating chamber may incorporate a heating coil 160, or some other heating element whereby heat is generated within the heating chamber.

In an embodiment of the present invention, wherein the upper manifold 2 and lower manifold 1 are be formed to have edges and sides that do not contact any portion of the heat transfer chamber and that do not form any hollow interior within either the upper manifold or the lower manifold, vapors generated from the content of the herb chamber will exit the herb chamber into the housing of the base unit generally. The vapors will therefore not be directed and may take longer to reach the manifold outlet 1004 and the conduit section that embodiments that have vapor director elements therein. However, the vapors may be cooler in this type of embodiment when the vapors reach the conduit section than in embodiments of the present invention that incorporate vapor director elements. The vapors may further reach the conduit section in a less concentrated volume than in embodiments of the invention wherein the vapors are directed from the herb chamber into the hollow interior of the upper manifold and therefrom into the manifold outlet and the conduit section. As discussed herein, the present invention may be configured to provide the user with less and more concentrated, variant cool temperatures, and higher and lower volumes of vapors. Therefore, the configuration of the upper manifold and lower manifold as shown in FIG. 9 may be incorporated in embodiments of the present invention that provide a user with a lower concentration, cooler, and lower volume, of vapors than other embodiments.

As shown in FIG. 10, the manifold and other elements may be positioned within the housing 1005 of the base unit 30. The housing will be configured to enclose the manifold and other elements shown in FIG. 4, with the exception of the whole of the outlet tube and the conduit section shown in FIG. 4. The housing of the base unit may be of any shape or configuration, and for example may be configured in accordance with the requirements of the function of the embodiment of the present invention.

The housing of the base unit may include upper and sidewalls, and engage with and connect to the base 18. Alternatively, the housing of the base unit may include upper, side and lower walls, and the base 18 may be incorporated within the housing of the base unit. The upper wall of the housing of the base unit will be parallel, or virtually parallel to the bottom of the beverage dispenser when the invention is fully assembled. In some embodiments of the present invention, the bottom of the beverage dispenser will be connectable to the upper wall of the housing of the base unit. In some embodiments of the present invention the housing of the base unit 30 may not incorporate an upper wall, and the bottom of the beverage dispenser 10 may be directly connected to the sidewalls of the housing when the invention is fully assembled.

Figure 11:
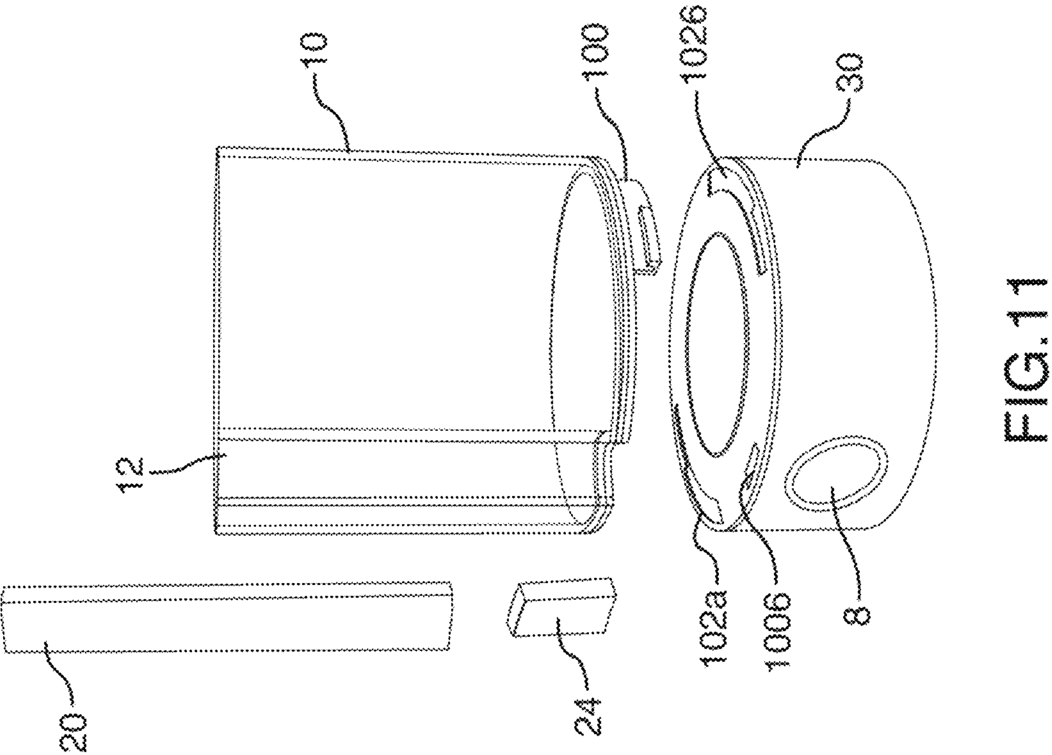
FIG. 11 is an exploded view of elements of the beverage and vapor dispenser, of an embodiment of the present invention.

In some embodiments of the present invention the conduit section is connected to the manifold outlet, directly or via the outlet tube, when the invention is fully assembled. As shown in FIG. 10, the housing of the base unit may be formed of transparent or semi transparent materials in some embodiments of the present invention. As shown in FIG. 11, in other embodiments of the present invention, the housing of the base unit may be formed of an opaque, or translucent material.

As shown in FIG. 11, the base unit 30 is removable from the beverage dispenser 10, and the conduit section 20 is further removable. The beverage dispenser and conduit section can be cleaned when removed, or these elements can be replaced when necessary due to damage or wear and tear. The connection between the beverage dispenser and the base unit may be achieved through a variety of attachments, for example, such as one or more extending sections 100 integrated with the bottom of the beverage dispenser, being insertable into slots 102*a*, 102*b* in the upper wall of the housing of the base unit. The extending sections and slots may be configured such that when connected the beverage dispenser and base unit may be locked into a non-fixed connection, or otherwise firmly connected.

Any connection between the beverage dispenser and the base unit will be non-permanent and detachable. A skilled reader will recognize that there are several types of mechanisms that may be incorporated into the base unit housing and/or beverage dispenser, whereby the based unit and beverage dispenser may be attached and detached as required for the purpose of the present invention.

The conduit section 20 may be inserted into the outlet 1006 formed in the base unit housing and connected to the manifold outlet 1003 that is aligned with the outlet 1005. The connection between the manifold outlet and the conduit section may be formed by the conduit section being inserted into the manifold outlet, or by some other connection mechanism. Alternatively, an outlet tube 24 may be inserted into the outlet 1006 formed in the base unit housing and connected to the manifold outlet 1003 that is aligned with the outlet 1006. The connection between the manifold outlet and the outlet tube may be formed by the outlet tube being inserted into the manifold outlet, or by some other connection mechanism. Vapor may flow from the base unit, through the outlet into the outlet tube, and through the outlet tube into the conduit section.

Figure 12:
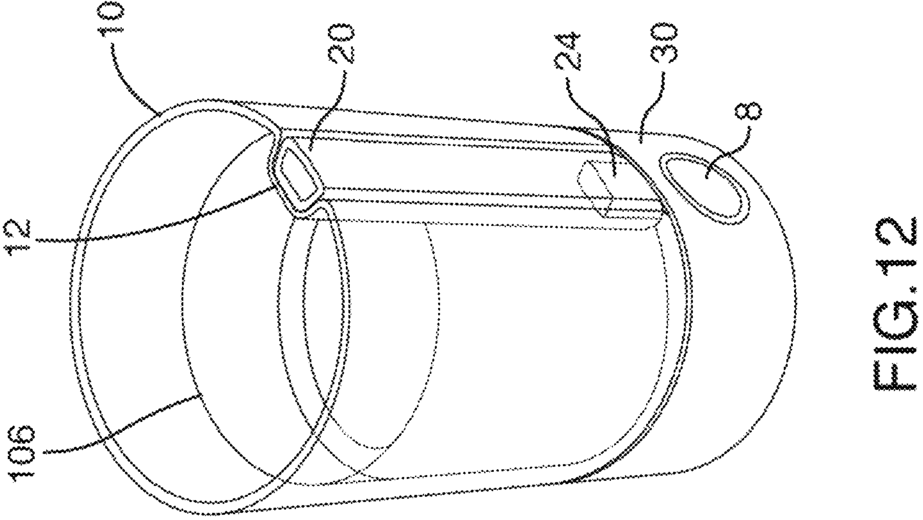
FIG. 12 is an upper-side perspective view of the beverage and vapor dispenser, of an embodiment of the present invention, wherein the beverage dispenser and vaporizer unit are in operation.

As shown in FIG. 12, when the present invention is fully assembled, the beverage dispenser 10 may contain liquid 106, that may be a beverage or some other liquid. Further, when the present invention is fully assembled, the base unit may be activated, through use of the heat activation button, to heat the content of the herb chamber within the base unit, and vapor therefrom may be released from the base unit into the conduit section 20 connected thereto.

Figure 13:
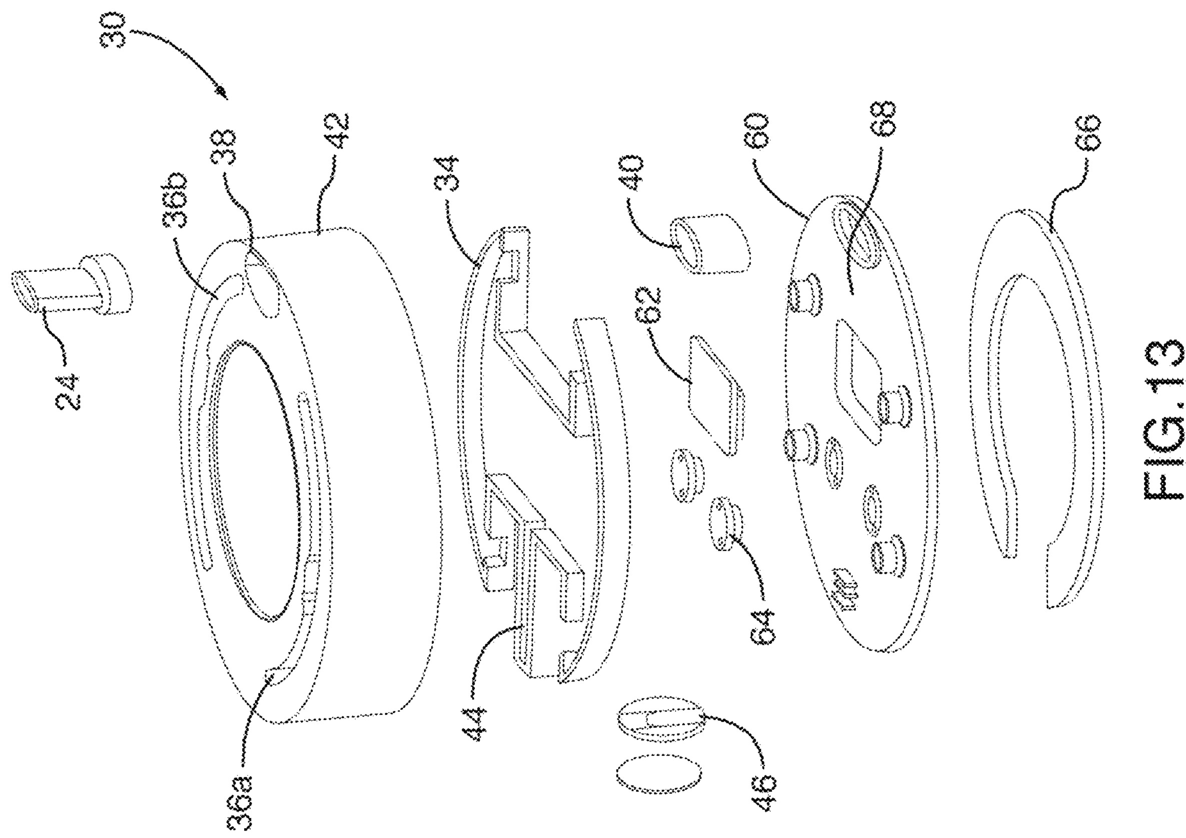
FIG. 13 is an exploded view of elements of the vaporizer unit, of an embodiment of the present invention.

The base unit incorporates multiple elements that can be easily detached as required for the purpose of cleaning or fixing the base unit. The elements of the base unit and the configuration thereof can vary in accordance with embodiments of the present invention for particular purposes, as discussed herein and as shown in the drawings. As an example, an embodiment of the base unit, as shown in FIG. 13, incorporates an outlet tube 24, that may be formed of plastic, glass, metal, silicone or some other material and may be transparent, translucent or opaque. The housing 42 of the base unit may be formed of plastic, glass, metal, silicone, aluminum or any other material operable to hold its shape at high degrees of heat, and may be transparent, translucent or opaque. The housing 42 may incorporate slots, 36*a*, 36*b* or other means whereby the base unit is attachable to a beverage dispenser. The beverage dispenser may have extruding sections attached to or incorporated in the bottom of the beverage dispenser that are shaped to fit within the slots 36*a*, 36*b*. When the extruding sections are fit within the slots the beverage dispenser may be attached to the housing of the base unit. In some embodiments the slot and extruding section may be more securely attached by twisting or pressure force being exerted upon the connection between the extruding sections and the slots. Other connection mechanisms may be incorporated in the housing and/or the beverage dispenser, or there-between, to create a detachable connection between the housing and the beverage dispenser with the present invention is assembled. Any such connection between the housing and the beverage dispenser will be detachable.

The housing 42 incorporates an outlet element 38. The elements described below as being shown in FIG. 13 are positioned within the housing.

An herb chamber/upper manifold 34 may be configured to incorporate a herb chamber 44 within the upper manifold and may be formed out of plastic, glass, metal, silicone, aluminum or any other material operable to hold its shape at high degrees of heat, and may be transparent, translucent or opaque. An upper manifold door 46 is attachable to the upper herb chamber/upper manifold to provide access to the herb chamber, whereby content can be put into and removed from the herb chamber. A heating element 40 may be positioned on a base element 66 and below a lower manifold element 60. The lower manifold element may incorporate heat transfer element 62 that operates to transfer heat to the herb chamber. The lower manifold may further incorporate a heat manifold outlet element 68, operable to be connected to the outlet tube. The elements of this configuration of an embodiment of the base unit may be connected by screws 64, pins or by other connection mechanisms.

The embodiment of the base unit shown in FIG. 13 is attachable to a beverage dispenser and a conduit section, in the manner described herein for other configurations of the base unit. The elements of this embodiment further function in the same manner as described herein for other embodiments of the base unit, such that: content can be inserted into the herb chamber; the heating element can be activated to begin to heat up; the heat transfer element can assist in transferring the heat from the heating element to the herb chamber; the content of the herb chamber once heated will generate vapors; the vapors can be transferred from the base unit through the manifold outlet element into the outlet tube that is positioned to be connected to the manifold outlet element and extends through the outlet element 38; and the outlet tube is connectable to a conduit section whereby the vapors are provided to a user.

Figures 14, 15:
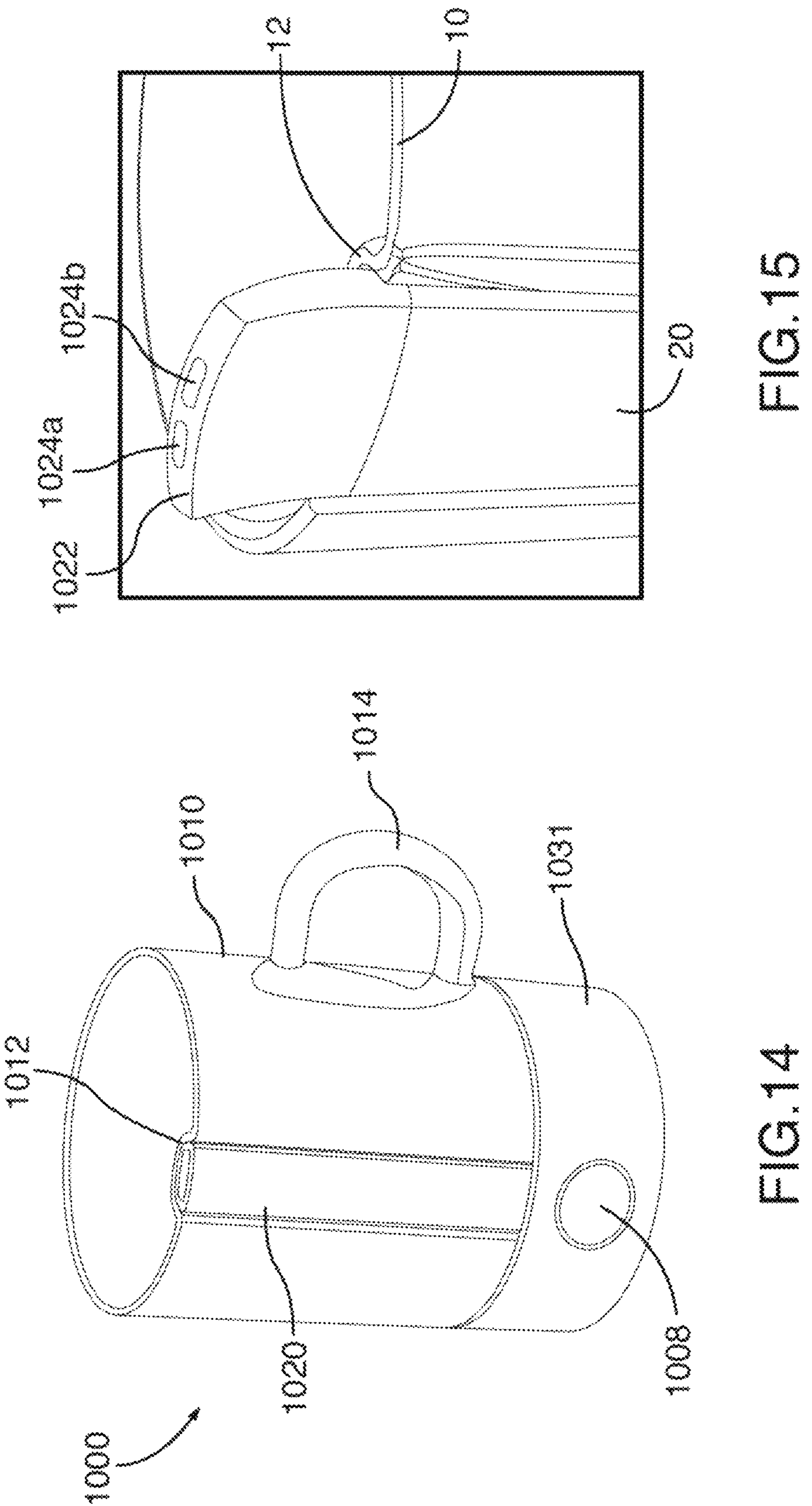
FIG. 14 is a front perspective view of the beverage and vapor dispenser, of an embodiment of the present invention.
FIG. 15 is a side perspective view of a portion of the conduit section and a tip incorporated in the beverage and vapor dispenser, of an embodiment of the present invention.

The beverage dispenser may be any type of beverage dispenser, including any type of cup that a user can drink a beverage from. As shown in FIG. 16, the beverage dispenser may be a glass or cup. As shown in FIG. 14, the beverage dispenser may be shaped as a mug 1010 having a handle 1014 attached thereto. The mug may be configured to incorporate a mug indentation 1012, wherein a mug conduit section 1020 may be positioned to be parallel or virtually parallel to a sidewall of the mug. The mug is attachable to a mug base section 1031, that incorporates a mug heat activation button 1008 whereby content of the mug base section can be heated to produce vapor that will be delivered to the user via the mug conduit section.

As shown in FIG. 15, in some embodiments of the present invention, the conduit section may have a tip 1022 attached to its uppermost end, being the end from which the user will inhale the vapors by nose or mouth. The tip 1022 may incorporate one or more holes 1024*a*, 1024*b* wherefrom vapor will be expelled from the conduit section. The tip may thereby control the volume of vapor delivered to a user via the conduit section, as the number of, and size of, such holes in the tip will either limit (if there are small and few holes), or augment (if there are large and many holes) the volume of vapor delivered to the user. For example, the tip shown in FIG. 15 incorporates two holes, whereas the tip shown in FIG. 16*a* incorporates four holes (1024*a*-1024*d*). Thus, the tip may assist with ensuring the user receives an appropriate volume of vapor, in accordance with the use of the vapor by the user. For example, if the vapor has medicinal properties, a particular volume of vapor should be delivered to the user when the user inhales vapor from the conduit section. The configuration of the tip may ensure the correct volume of vapor is delivered to the user.

The tip is removable from the conduit section. Multiple tips having different configurations may be attachable to the conduit section, although only a single tip may be connected at a time. Each tip may be configured to be used with a different type of vapor produced by different types of content in the herb chamber or to deliver a different volume of vapor passing through the tip to a user. The tips thereby ensure that the invention can be used with different types of content in the herb chamber and that the user will receive the appropriate volume of vapor, as may be appropriate relating to such content or relating to other requirements of the user.

The tips may further allow for a hygienic method for the invention to be used by multiple users, as each user may use a different tip attached to the conduit section when that person inhales vapor from the conduit section by nose or by mouth. This can help to avoid disease or other illness to be transferred to multiple persons as may occur due to use of the same tip by multiple users.

Figure 24:
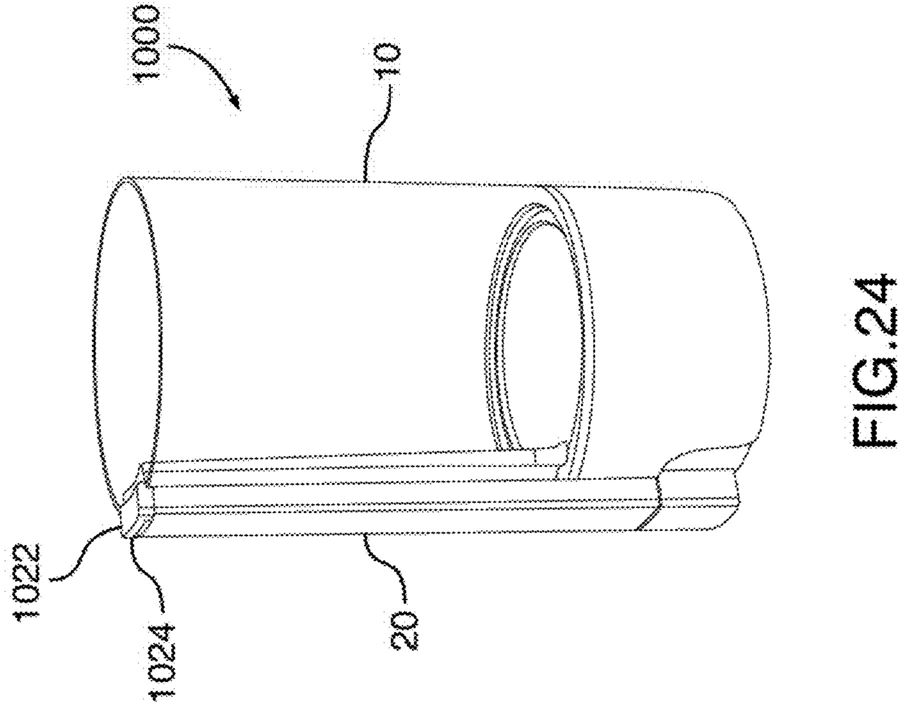
FIG. 24 is a side perspective view of the beverage and vapor dispenser having a side vapor release, of an embodiment of the present invention.
Figure 23:
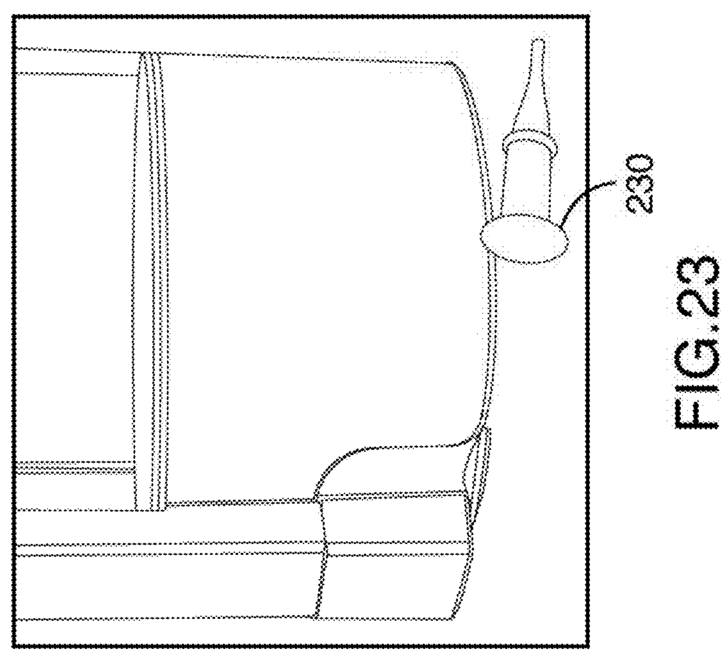
FIG. 23 is a side perspective view of herb stirrer, of an embodiment of the present invention.

As shown in FIG. 24, the tip 1022 may be positioned at, or virtually at, the height of the beverage dispenser. The tip may further incorporate one hole 1024, or multiple holes, that permit vapor to be expelled from a side of the conduit section 20.

Figures 16A, 16B:
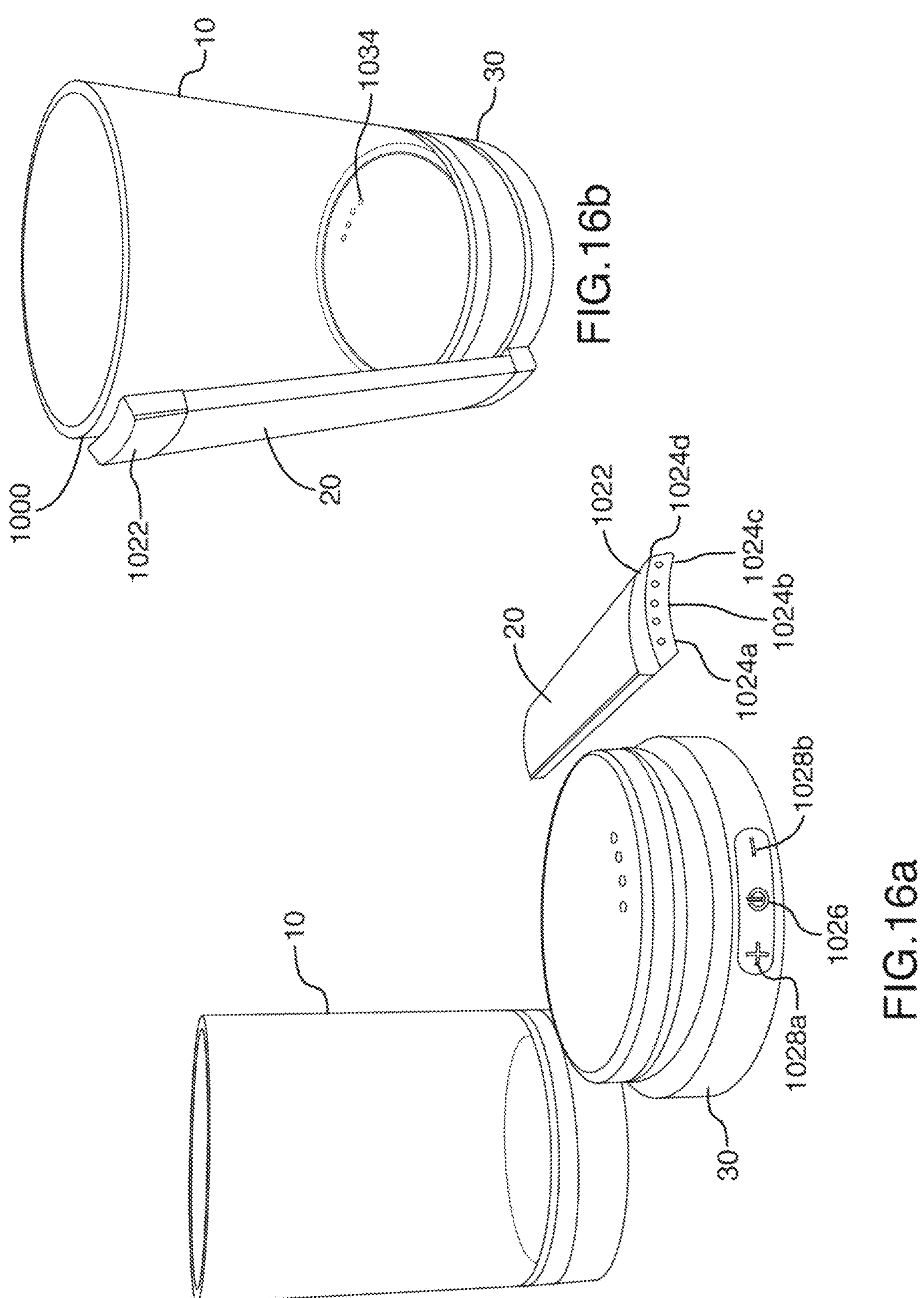
FIG. 16*a* is an exploded view of elements of the beverage and vapor dispenser, of an embodiment of the present invention.
FIG. 16*b* is a perspective view of the beverage and vapor dispenser, of an embodiment of the present invention.
Figures 18A, 18B:
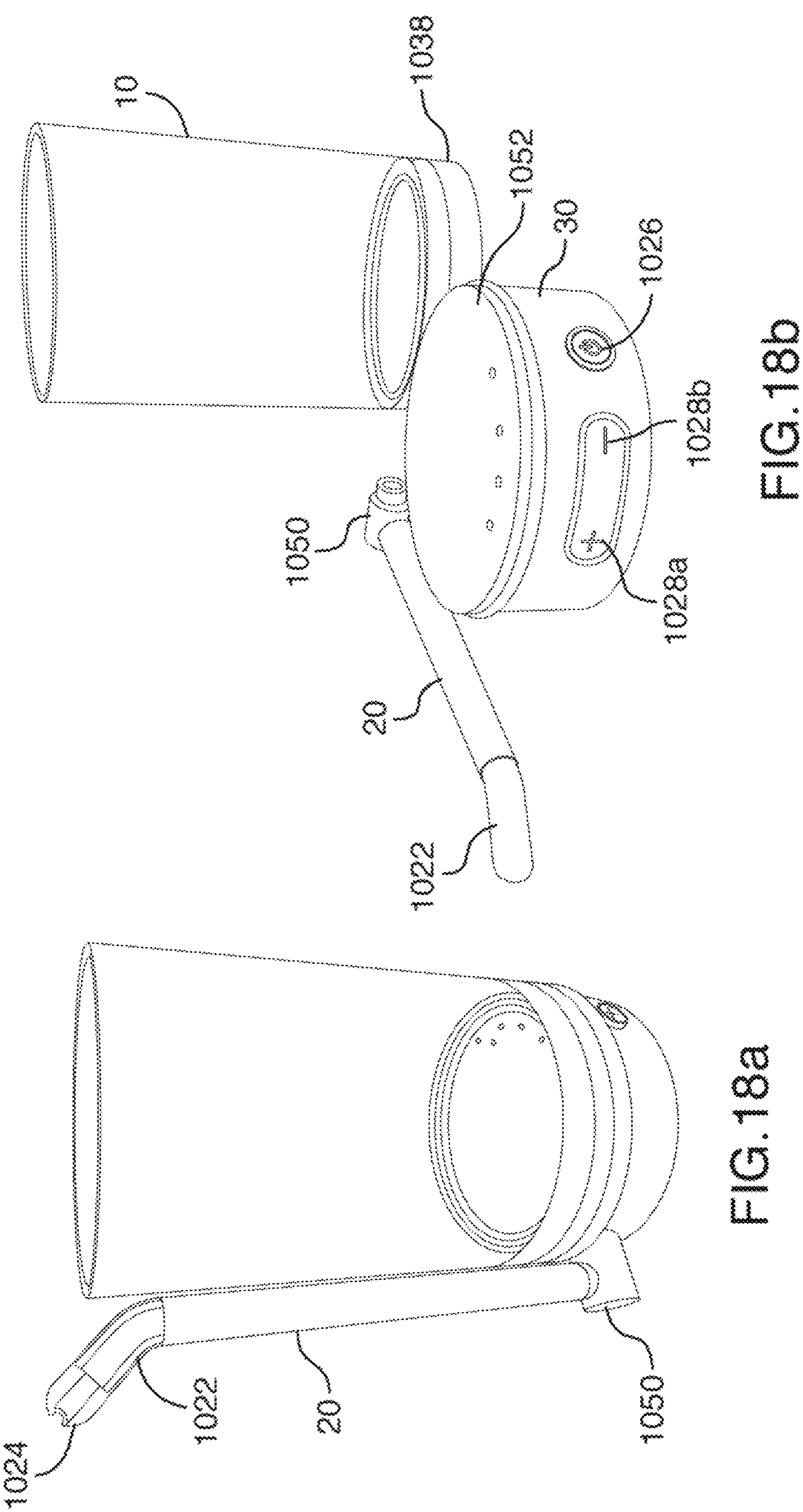
FIG. 18*a* is a perspective view of the beverage and vapor dispenser, of an embodiment of the present invention.
FIG. 18*b* is an exploded view of elements of the beverage and vapor dispenser, of an embodiment of the present invention.

FIG. 16 shows the beverage dispenser 10, conduit section 20 with a tip 1022 attached thereto, and base unit 30 unassembled. The base unit incorporates a heat activation button that allows a user to activate the heat by pressing activation button 1026, to increase the heat by pressing increase button 1028*a* and to decrease the heat by pressing decrease button 1028*b*. The heat decrease and heat increase buttons can be used while the heating chamber is activated to increase or decrease the heat generated by the heating coils, or the heat decrease and heat increase buttons can be used when the heating chamber is not activated to set a maximum temperature that the heating coils should heat to the next time the heating chamber is activated. This embodiment of the present invention is shown assembled in FIG. 16*b*. As shown in FIG. 18*b*, in other embodiments of the present invention the activation button 1026, increase button 1028*a* and decrease button 1028*b* may be distinct buttons in the base unit 30.

Figures 17A, 17B:
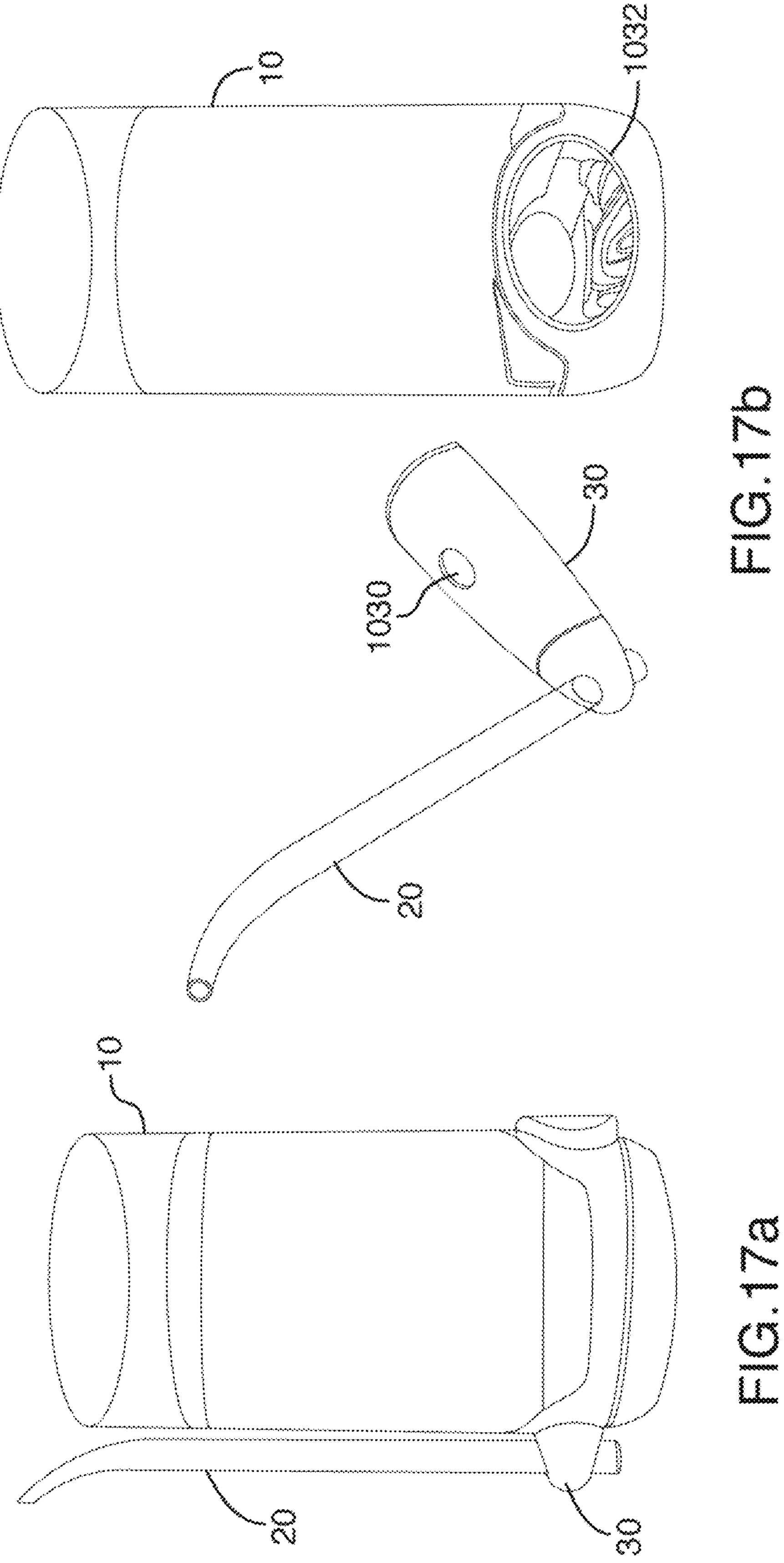
FIG. 17*a* is a perspective view of the beverage and vapor dispenser, of an embodiment of the present invention.
FIG. 17*b* is an exploded view of elements of the beverage and vapor dispenser, of an embodiment of the present invention.

As shown in FIG. 17*a*, the base unit 30 may be configured such that the housing of the base unit fits within an enclosed hollow section, forming a tunnel, in the lower section of the beverage dispenser 10. The conduit section 20 may be connected with the base unit 30 and extend therefrom. In this embodiment of the present invention, the conduit section does not fit within any indentation in the beverage dispenser and does not necessarily need to be positioned either parallel or virtually parallel to the beverage dispenser, although it may be so. In this embodiment the conduit section may be positioned at a distance from the beverage dispenser.

The base unit 30 and beverage dispenser 10 of this embodiment are shown to be disassembled in FIG. 17*b*. The beverage dispenser is configured to incorporate an enclosed tunnel 1032 in its lower section. The enclosed tunnel can be positioned in other sections of the beverage dispenser in other embodiments of the present invention. The base unit 30 incorporates a screen 1030 that indicates information, such as the temperature of the vapor, or the temperature of the heating chamber. This screen could indicate other information such as the amount of time until vapor is produced, or until the heating chamber is fully heated, or any other information. The user can read the information on the screen when the base unit is removed from the beverage dispenser, and if the enclosed tunnel is formed of transparent material, it may be possible for the user to view the screen when the base unit is inserted within the enclosed tunnel of the beverage dispenser.

In another embodiment of the present invention, the herb chamber 1048 may be attached to the conduit section 20. In such an embodiments, the chamber tray 1042 may be removable from the herb chamber. The content, such as herbs, will be placed into the chamber tray. The chamber tray can be emptied or cleaned when it is removed from the herb chamber, or it can be filled with herb content.

As shown in FIGS. 18*a* and 18*b*, in an embodiment of the present invention, the conduit section 20 may incorporate an outlet connection 1050, and the base unit may incorporate a side outlet whereby vapor generated within the base unit may be dispersed from the base unit. The outlet connection of the conduit section is connectable to the side outlet of the base unit. Once so connected the vapor within the base unit will be directed through the side outlet and into the conduit section, whereby it will be delivered to the user. In this embodiment the conduit section is positioned at a distance from the beverage dispenser. The beverage dispenser may not incorporate any indentation configured in relation to the conduit section. The conduit section does not need to be positioned either parallel or virtually parallel to the beverage dispenser in this embodiment, although it may be so.

In embodiments of the present invention, the conduit section may not extend to the full height of the beverage dispenser, as shown in FIG. 18*a*. The tip 1022 attached to the conduit section may be positioned at an angle to the conduit section when connected to the conduit section.

Figures 19A, 19B:
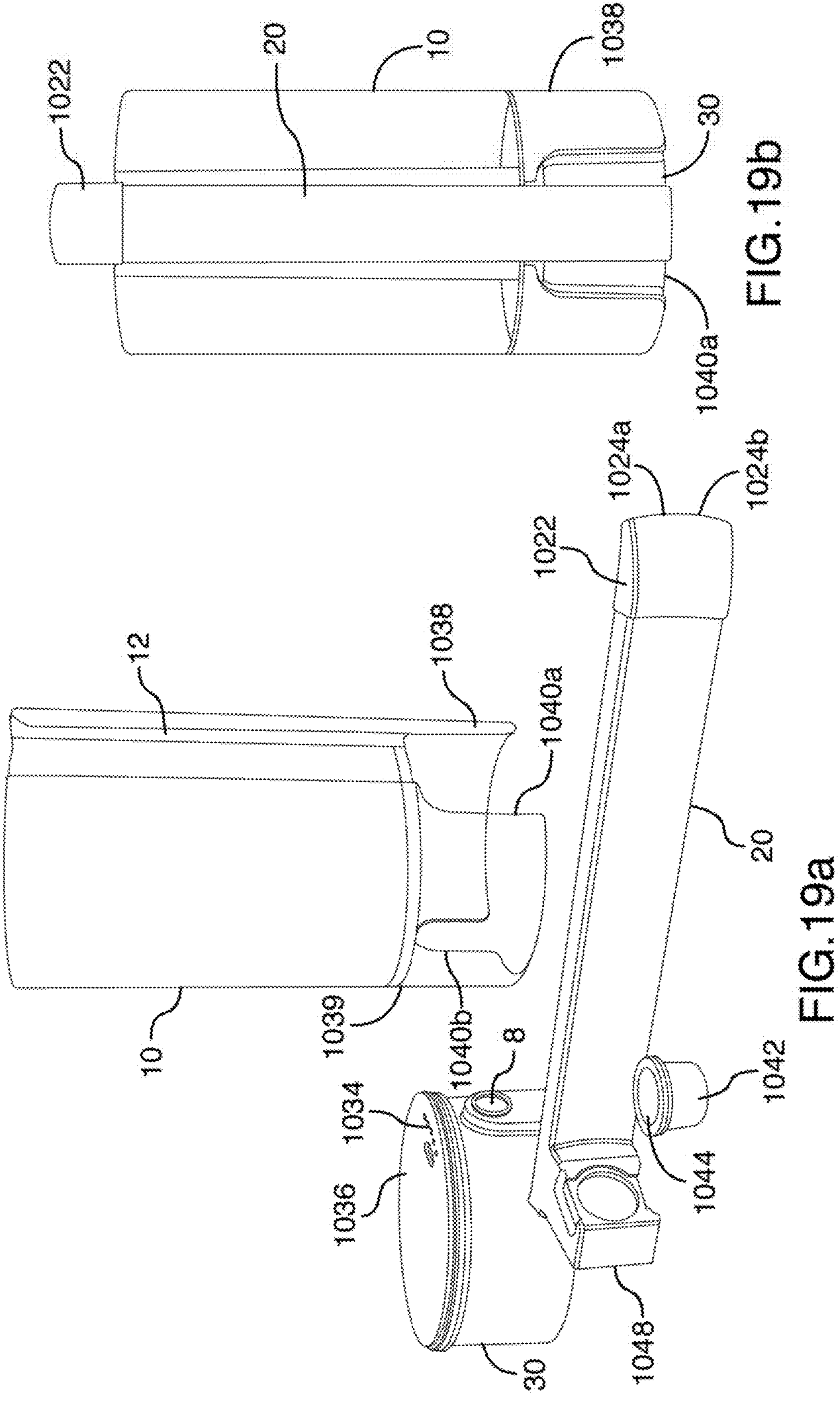
FIG. 19*a* is an exploded view of elements of the beverage and vapor dispenser, of an embodiment of the present invention.
FIG. 19*b* is a perspective view of the beverage and vapor dispenser, of an embodiment of the present invention.

As shown in FIG. 19*a*, the chamber tray 1042 may be configured to be removably integrated within an herb chamber 1048 in the conduit section 20. The chamber tray may be formed of material with low thermal conductivity properties such that the chamber tray may dissipate heat, such as aluminum, steel or titanium. Alternatively, the chamber tray may be formed of material with high thermal conductivity properties such that the chamber tray may retain and concentrate heat, and such a chamber tray may be utilized with herb content that is an oil or any other type of herb content requiring increased heating to vaporize. An herb may be placed within the interior 1044 of the chamber tray 1042. When this embodiment of the present invention is assembled, the conduit section is integrated with a base unit 30 and a beverage dispenser 10. The wall of the base unit that is positioned parallel or virtually parallel to the bottom of the beverage dispenser when the base unit is attached to the beverage dispenser incorporates a charging port 1036. The charging port may be positioned on any wall of the base unit. When a cable is connected between the charging port and an electrical outlet the battery of the base unit may be charged. The battery is connected to the heat activation button and/or the heating coils. The battery provides the power necessary for the heating coils to generate heat.

The charging port may be water resistant and may incorporate a barrel jack connection or a USB connection. Embodiments of the present invention may further incorporate wireless charging functionalities, such as elements incorporated in the base unit whereby the battery may be charged when the base unit is in close proximity to or direct contact with a wireless charging pad.

The wall of the base unit that is positioned parallel or virtually parallel to the bottom of the beverage dispenser when the base unit is attached to the beverage dispenser incorporates one or more lights 1034. The one or more lights are operable to indicate operating modes of the base unit. For example, if multiple lights are utilized, the number of lights lit up may indicate the level of heat generated by the heating coils, with one light being low heat and each additional light indicating a higher level of heat, such that when all lights are lit the highest level of heat is indicated. The lights may further indicate the maximum temperature setting for the heating coils, such that one light being lit indicates that the maximum temperature setting for the heating coils is low, two lights being lit indicates a higher temperature setting for the heating coil, and so on. The one or more lights may be LED lights, RGB lights or any other type of light. If the lights are colour the colour of the lights may further indicate information regarding the function of the vaporizer unit elements of the base unit to a user.

The one or more lights may be visible to a user when the present invention is assembled, as shown in FIG. 16*b*. For example, as shown in FIG. 28, if the bottom of the beverage dispenser is transparent and the ledge section 222 is positioned so that it does not cover the one or more lights, or a ledge indentation 224 is incorporated in the ledge section 222 whereby the one or more lights remain uncovered, the lights may be visible to the user when the present invention is assembled.

The one or more lights may be controlled by the increase button 1028*a* and decrease button 1028*b*, in the manner discussed herein, or by pressing the heat activation button. In embodiments of the present invention, the one or more lights may be replaced by a screen showing numbers or words that indicate the heat produced by the heating coils, or the temperature setting for the heating coils, as shown in FIG. 17*b*.

Figures 28, 29:
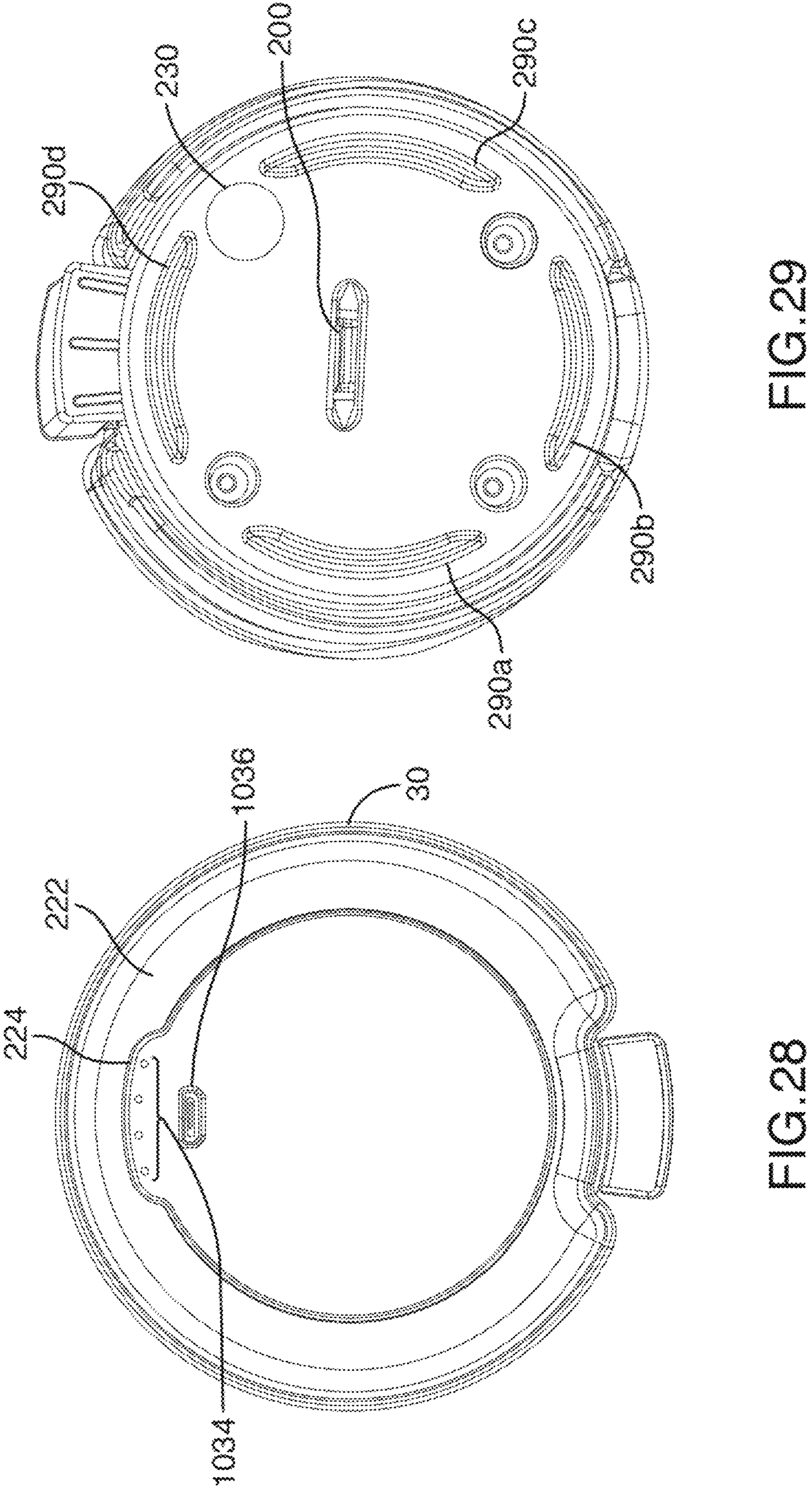
FIG. 28 is a top view of a base unit, of an embodiment of the present invention.
FIG. 29 is a base view of a base unit, of an embodiment of the present invention.

As shown in FIG. 28, the one or more lights 1034 and the charging port 1036 may be positioned in the wall of the base unit that is positioned parallel or virtually parallel to the bottom of the beverage dispenser when the base unit is attached to the beverage dispenser. The one or more lights 1034 or the charging port 1036 may be positioned in any wall of the base unit.

In embodiments of the present invention, the herb chamber is connected to the conduit section and is insertable into the base unit, as shown in FIG. 19*b*. In such an embodiment the vapor will be directed from the herb chamber directly into the conduit section. Such vapor will be provided to the user. A mechanism to induce a particular flow of the vapor (e.g., convective flow, fans, configuration of elements of the base unit, or other mechanisms) or walls enclose the heating chamber and herb chamber elements in close proximity to the conduit section, whereby no or minimal vapor can travel in the base unit other than towards the conduit section, may be utilized to ensure that all or virtually all of the vapor generated is delivered to the user through the conduit section.

In embodiments of the present invention, the beverage dispenser may incorporate wall extensions 1038, being walls that extend below the bottom section 1039 of the beverage dispenser. The wall extensions may form a type of skirt extending from the bottom section of the beverage dispenser or the wall extensions may be removably connected to the bottom of the beverage dispenser. In such embodiments of the present invention, the beverage dispenser is attached to the base unit by the wall extensions that surround the base unit when the beverage dispenser is positioned above the base unit and the present invention is assembled. The base unit circumference may be equivalent or slightly less than the circumference of the interior side of the wall extensions. The size of the circumference of the base unit and the interior side of the wall extensions will be configured to cause the extension walls to surround the base unit with no or minimal space between the exterior walls of the base unit and the interior walls of the walls extensions. The result being that the wall extensions and base unit are connected by friction existing between the exterior walls of the base unit and the interior walls of the wall extensions. A snug fit is thereby formed between the base unit and the wall extensions and this friction fit causes the beverage dispenser to be attached to the base unit by the wall extensions.

The wall extensions may incorporate one or more cutouts where necessary in relation to elements in the exterior walls of the base unit. For example, a cutout 1040*b* may fit around the heat activation button, and a cutout 1040*a* may fit around the conduit section incorporating the herb chamber where the herb chamber is inserted into a side outlet of the base unit, as shown in FIG. 19*b*.

As shown in FIG. 19*b*, the wall extensions 1038 may be configured so that they cover only a portion of the exterior walls of the base section 30, when the beverage dispenser 10 is connected to the base section. In such an embodiment, the base section may incorporate a decreased circumference element 1052 in a portion of the upper exterior wall wherein the circumference of the exterior walls is less than the circumference of the rest of the exterior walls of the base unit. The decreased circumference may be shaped as ledge, an L-shaped section formed in the exterior wall, or an angled or sloping wall. The wall extensions are configured to be of a larger circumference that the circumference of the decreased circumference element, such that the wall extensions engage with the decreased circumference element of the base unit, to form a friction based connection between the beverage dispenser and the base unit.

Figures 20A, 20B:
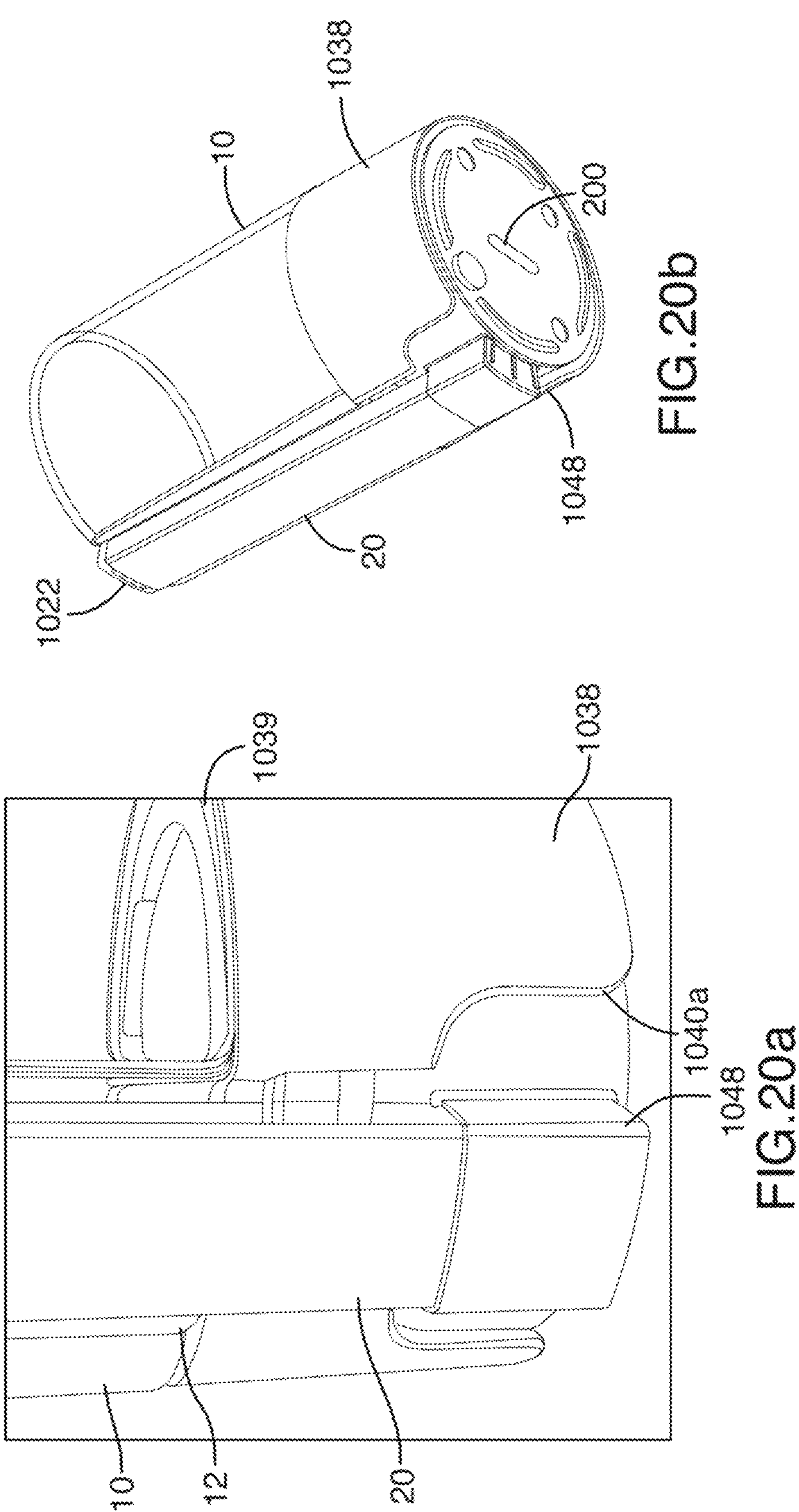
FIG. 20*a* is a rear perspective view of the beverage and vapor dispenser, incorporating a wall extension, of an embodiment of the present invention.
FIG. 20*b* is a bottom perspective view of the beverage and vapor dispenser, incorporating a wall extension, of an embodiment of the present invention.
Figure 20D:
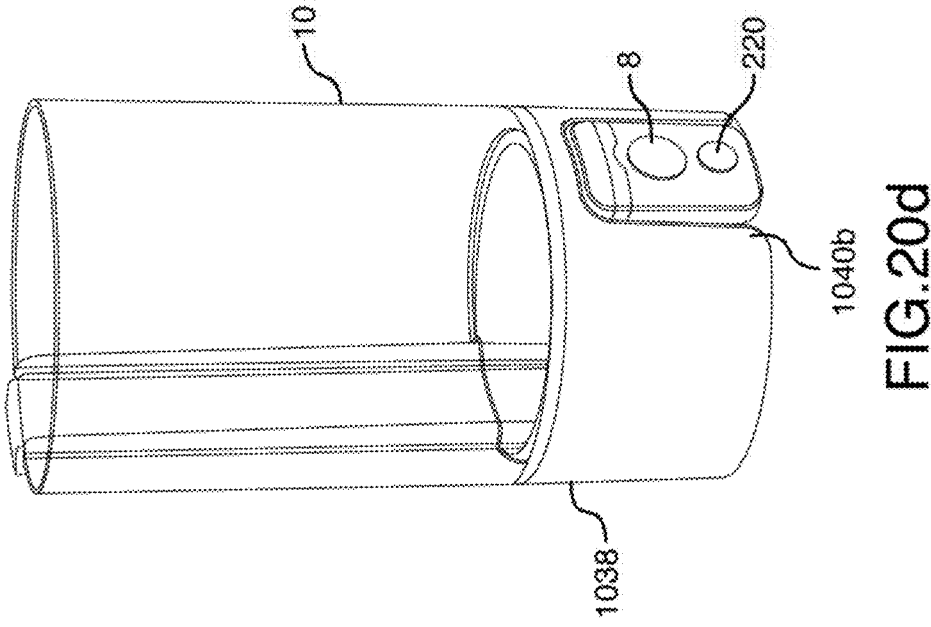
FIG. 20*d* is a front perspective view of the beverage and vapor dispenser, incorporating a wall extension, of an embodiment of the present invention.
Figure 20C:
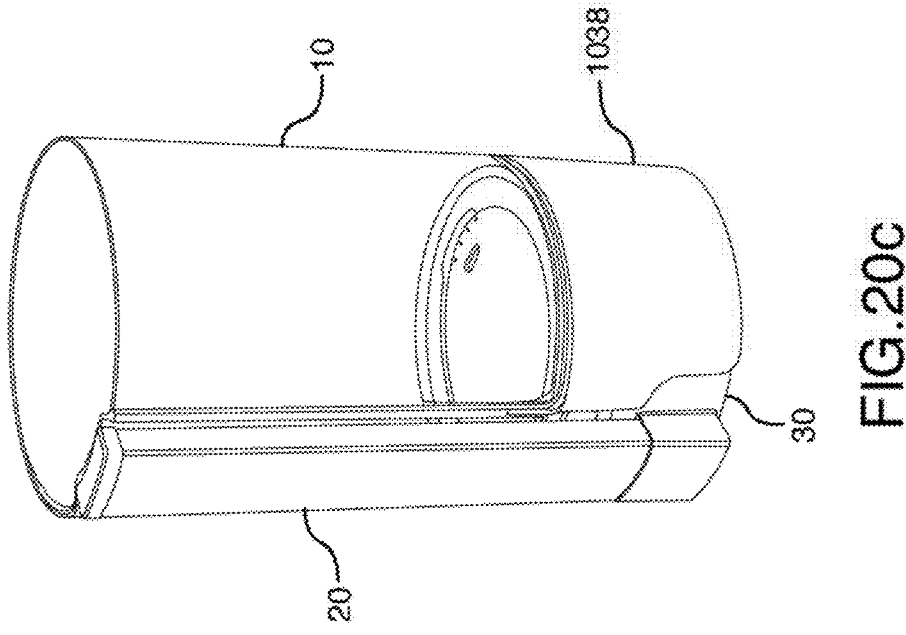
FIG. 20*c* is a side perspective view of the beverage and vapor dispenser, incorporating a wall extension, of an embodiment of the present invention.

As shown in FIGS. 20*a*, 20*b* and 20*c*, the conduit section 20 having an herb chamber 1048 incorporated therein, is insertable into the base unit 30. A cutout 1040*a* is formed in the wall extensions 1038 the directly extend from the beverage dispenser 10 or that are attached to the beverage dispenser. The cutout causes the wall extensions to surround, but not cover the area where the conduit section is inserted into the base unit.

As shown in FIG. 20*b*, an air inlet 200 may be formed in the bottom of the base section, whereby air can flow into or out of the base unit. In embodiments of the present invention, when a user draws air into the conduit section, such as by sucking on the conduit section or the tip attached thereto, air will be caused to flow into the air inlet. This drawing of air into the conduit section and inflow of air into the air inlet may be utilized with the heat generated by the heating chamber to induce or increase the efficiency of convection heating within the heating chamber and the direction of that heat to the herb chamber.

As shown in FIG. 20*d*, a cutout 1040*b* is formed in the wall extensions 1038 of the beverage dispenser 10 that cause the wall extensions to surround, but no cover the area where the heat activation button 8, and any other controls 220, such as temperature controls or other controls for the base unit, are positioned in the base unit. Other cutouts may also be formed in the wall extensions in relation to other elements formed in the base unit side walls.

Figures 21, 22:
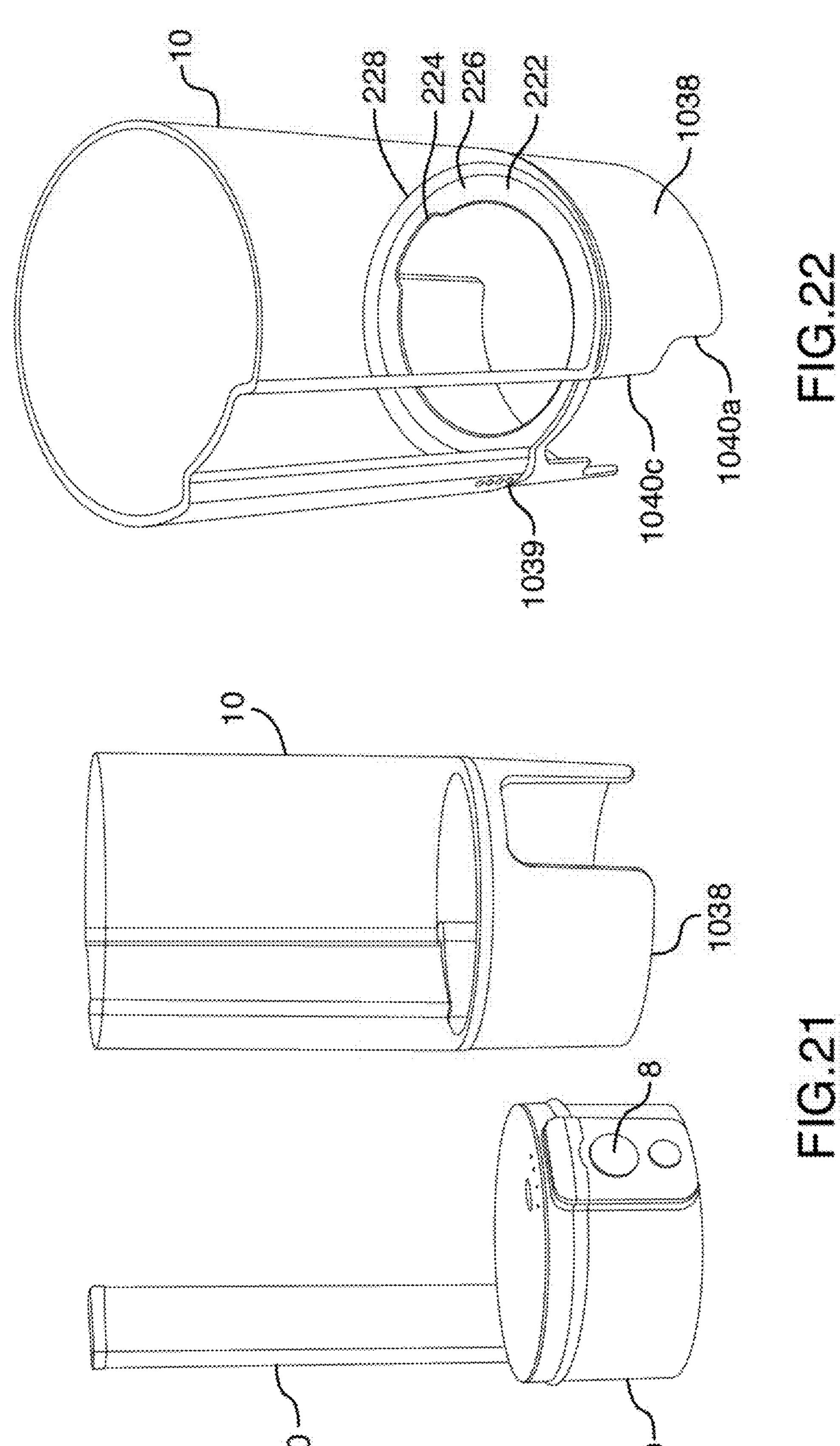
FIG. 21 is an exploded view of the beverage dispenser incorporating a wall extension and vaporizer unit, of an embodiment of the present invention.
FIG. 22 is a top perspective view of the beverage dispenser incorporating a wall extension, of an embodiment of the present invention.

As shown in FIG. 21, the conduit section 20 may be inserted into the base unit 30 before the beverage dispenser 10 is attached to the base unit. The wall extensions 1038 and a cutout 1040*a* therein will permit the wall extensions to be fitted around portions of the base unit, including the connection of the conduit section and the base unit, as described herein.

Any cutout sections in the wall extensions 1038, such as a cutout section 1040*a* to fit around the connection of the conduit section to the base unit, as may extend below the conduit indentation 12 in the beverage dispenser, may be configured to be of varying widths. For example, such a cutout may incorporate a narrower width section 1040*c*. The variant shaping of the cutout sections may be configured to increase the portion of the wall extensions being in contact with the base unit housing when the beverage dispenser is connected to the base unit. The greater the amount of the base unit housing that is in contact with the wall extensions the greater the amount of friction that is created between the base unit and the wall extensions. Increased friction can generate a more secure connection between the base unit and the beverage dispenser when the present invention is assembled.

As shown in FIG. 22, the wall extensions may be configured to further incorporate a ledge section 222 that may be attached to the bottom of the wall extensions. One or more ledge indentations 224 may be formed in the ledge section 222. A sloping wall 226 may extend between the ledge section 222 and the wall extensions upper edge 228. The bottom of the beverage dispenser may be configured to fit within the sloping wall, or the ledge may be fixedly attached to the bottom section 1039 of the beverage dispenser. The ledge may be configured to cause a gap of empty space to exist between the bottom of the beverage dispenser and the top of the base unit housing. This gap assists in preventing, or minimizing, the effect of any heat generated by the heating chamber within the base unit upon the temperature of any liquid within the beverage dispenser.

In embodiments of the present invention, the materials from which the housing of the base unit and the beverage dispenser are formed can further ensure that heat generated by the heating chamber within the base unit does not affect the temperature of any liquid within the beverage dispenser. For example, one of, or both of, the housing of the base unit and the beverage dispenser can be formed of a material that does not conduct heat well, such as aluminum or other materials. As another example, an insulating layer can be incorporated in one of, or both of, the base unit and the beverage dispenser.

Figure 34:
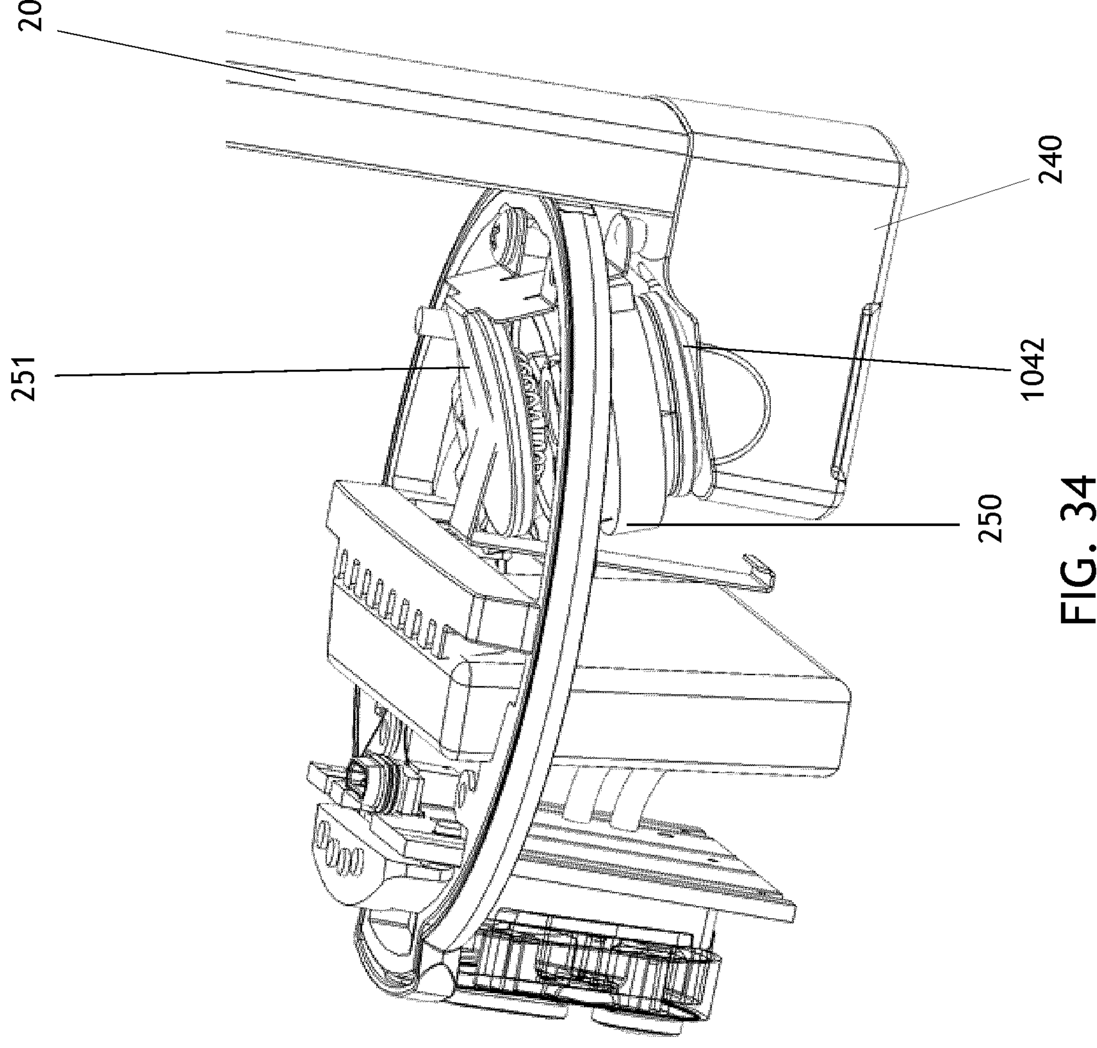
FIG. 34 is a sectional view of a beverage and vapor dispenser, of an embodiment of the present invention.

The heating coils of the present invention may further be sealed within a heating chamber formed of steatites, ceramic, or other materials. This sealed heating chamber will help to direct the heat to the herb within the chamber tray, and prevent heat from circulating widely within the base unit generally. The sealed heating chamber further ensures that the heat directed to the herb is such that it generates vapor at as cool of a temperature as possible, so that the herb will never burn. The sealed chamber may be suspended by one or more retention brackets 251, as shown in FIG. 34. The suspension of the heating chamber may prevent or reduce conduction heating of the surrounding materials and walls of the base unit. The suspended heating chamber may further ensure that the heat directed to the herb is such that it generates vapor at a user selected temperature on demand, so that the herb will not remain under constant heat when vapor is not being inhaled by the user. The convection heating of the herbs in the chamber tray may increase the longevity of use of such herbs, as only vapor that the user inhales by mouth will be generated in the herb chamber.

In embodiments of the present invention the heating chamber may heat sufficiently to generate vapor from an herb within a chamber tray in the base unit within 2-30 seconds or other short time frame. Embodiments of the present invention that generate vapor through convection heating, as described herein, will not require the heating chamber to remain heated for as long as prior art vaporizers to generate vapor from a herb, as vapor will only be generated when a user is inhaling vapor by mouth, and/or to be heated to temperatures as high as prior art vaporizers to generate vapor from a herb. In embodiments of the present invention, the optimal temperature for the function of the heating coils of the present invention may be between 320-450 degrees Fahrenheit.

The present invention may incorporate an herb stirrer 230. The herb stirrer may be used to stir the herbs in the chamber tray prior to the insertion of the chamber tray into the herb chamber. For example, the herb stirrer may be utilized if the herbs within the chamber tray are not granulated to an even consistent grind. Herbs that are ground to an even consistent grind will allow vapor to penetrate through all of the herbs, and create an even vaporization. The herb stirrer can be utilized to grind the herbs to an even consistent grind for this purpose. As another example, the herb stirrer can be utilized to move the herbs within the chamber tray. This may break down the herbs to affect even vaporization of the herbs. Stirring may further evenly distribute the herbs within the chamber tray, so that all or the majority of the herb content of the chamber tray will receive heat and be caused to generate vapor. If herb content is clumped within the chamber tray all of the dense clumped herb content may not receive heat, and therefore may not all be vaporized. The herb stirrer can assist with ensuring that the greatest amount of the herb content in the chamber tray is vaporized in the present invention.

Figures 25, 26, 27:
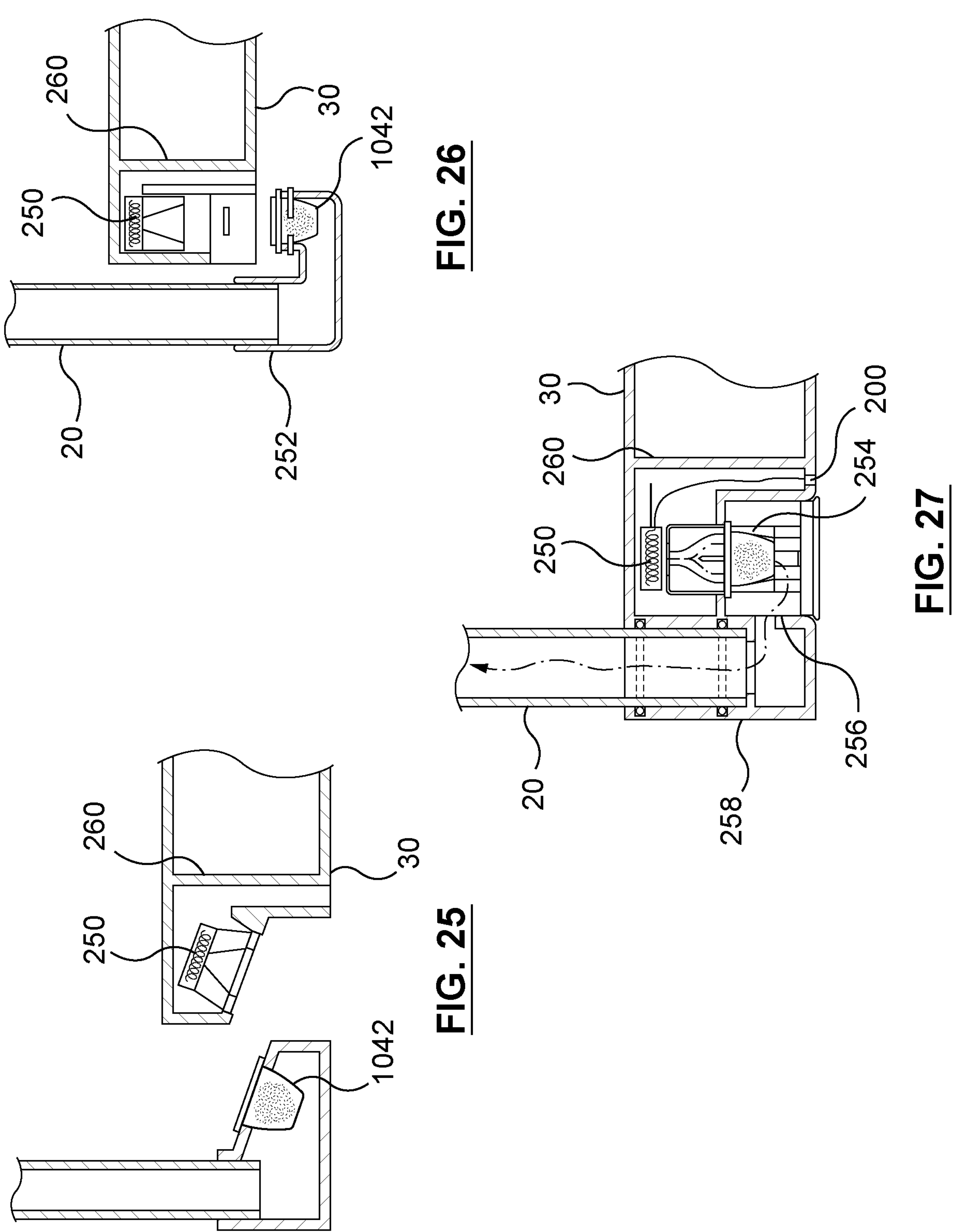
FIG. 25 is a side sectional side view of a conduit section disconnected from a base unit, of an embodiment of the present invention.
FIG. 26 is a sectional side view of a conduit section disconnected from a base unit, of an embodiment of the present invention.
FIG. 27 is a sectional side view of the base unit having a conduit section inserted therein, of an embodiment of the present invention.

As shown in FIG. 25, the herb content of the chamber tray 1042 may be heated by an upper heating chamber 250, positioned above the chamber tray. In such an embodiment of the present invention, the heating chamber is directly above the herb chamber, with limited space there-between. Vapor generated from the herb in the chamber tray of the herb chamber may flow directly into the conduit section. The upper heat chamber may be activated by an activation button, as described herein for other embodiments of the present invention. The upper heat chamber may further incorporate a heat transfer element adjacent to the herb chamber. The heat transfer element may be formed of a heat conductive material, and as the upper heating chamber releases heat, the heat conductive material transfers heat to the herb chamber, and thereby heats the herb chamber and the contents of the chamber tray.

The upper heating chamber may incorporate a heating coil, in the same manner as described herein. Air may enter the base unit through an air inlet in the base unit, as may for example be positioned in the base or bottom of the base unit. The upper heating chamber may operate with the air inlet to produce convection heating to heat herb content of the chamber tray. The convection heating may further be enhanced by a user drawing air through the conduit section (as occurs when the user sucks on the conduit section). This action by the user can compact the herb within the chamber tray, which assists in generating a smooth and pleasant tasting vapor. As discussed herein, the convection heating of the herb and/or a portion of the conduit section that incorporate a herb chamber, produces heating that generates vapor at a cooler temperature than prior art herbal vaporizers.

Generally air within the heating chamber will be slow moving. Air movement will be generated in the heating chamber when a user draws air through the conduit section and the heat activation button is utilized to activate the heater coils.

There are several possible configurations for a conduit section and base unit that operate with an upper heating chamber. As shown in FIG. 26, the lower conduit 252 incorporated in the conduit section 20 may be configured such that the chamber tray 1042 is positioned to be insertable into the bottom of the base unit. In such a configuration of the present invention, the heating chamber 250 may be positioned directly above and parallel or virtually parallel to the chamber tray when the conduit section is fit within the base unit. For example, in such an embodiment of the present invention, the lower conduit may be configured to be U-shaped, such that one side of the U is connected to the conduit section, the base of the U fits under the base unit 30, and the other side of the U has the herb chamber incorporated therein and is insertable into the base of the base unit or otherwise attachable to the base unit.

Another possible configuration for a conduit section and base unit that operate with an upper heating chamber is that the herb chamber incorporating a chamber tray 254 is positioned within the base unit 30. The upper heating chamber is positioned above the chamber tray to be parallel or virtually parallel to the top of the chamber tray. Air enters the base unit 30 through an air inlet 200 in the base of the base unit. The air and the upper heating chamber create convection heating of the herb content of the chamber tray. The conduit section is attached to the base unit whereby a base unit outlet 256 is aligned with and connected to an outlet tube 258, and the outlet tube is connected to the conduit section 20. The vapor generated by the upper heating chamber heating the herb content of the chamber tray flows through the base unit outlet into outlet tube and through the outlet tube into the conduit section to a user.

The base unit 30 may incorporate a protective wall 260 that completely or partially separates the heating chamber and herb chamber from other portions of the base unit. The protective wall, may act to protect elements on the other side of the protective wall from the heating chamber from the heat generated by the heating chamber, and may further limit the space where heat can disperse. This feature can act to assist in directing the heat to the herb in the chamber tray to generate vapor more quickly than prior art vaporizers. The protective wall creates a virtually total thermal isolation of the heat source in close proximity to the herbs. Additionally the wall can act to prevent vapor from escaping from the herb chamber in a direction away from the conduit section. The wall thereby can act to assist in directing all or virtually all of the vapor into the conduit section and to the user.

The base unit may have an air inlet formed therein whereby air can enter into the base unit. The air that flows in to the base unit through the air inlet is utilized in the convection heating generated by some embodiments of the present invention. In some embodiments of the present invention the air inlet 200 may be positioned in the bottom of the base unit 30, as shown in FIG. 29. The base unit may further be configured to incorporate a slot wherein the herb stirrer can be fit, such as is shown in FIG. 29. The herb stirrer 230 removable fits within such slot, which may be a hole or other indentation formed in the base of the housing of the base unit 30, and can thereby be stored with the base unit when the herb stirrer is not in use. One or more risers 290*a*, 290*b*, 290*c*, 290*d* may be formed in, or otherwise connected to, the bottom of the housing of the base unit. The risers may cause the present invention to be positioned with a gap between the bottom of the base unit and any surface that the present invention is positioned upon. The risers thereby ensure that air can reach the air inlet. This permits air flow into the air inlet whether the present invention is held by a user during use of the vaporizer, or placed upon a surface during use of the vaporizer. The risers may further function to ensure the air inlet is not blocked wholly or partially by any debris or liquid that may be located beneath the base unit. The risers may also be configured in relation to the conduit section that connects with the base or bottom of the base unit, such as is shown in FIG. 26.

In another embodiment of the present invention, as shown in FIG. 30, the beverage dispenser 10 may be configured to incorporate base sloping walls 232 near the bottom section 1039 of the beverage dispenser. The base sloping walls 232 may be configured to fit within sloping walls 226 extending between a ledge section 222 and the wall extensions upper edge 228 in wall extensions 1038. The configuration of the base sloping walls 232 and the sloping walls 226 may cause the wall extensions 1038 to fit snugly with the beverage dispenser and thereby be attached. The snug fit will be generated by friction between the base sloping walls 232 and the sloping walls 226, such that the more friction therebetween the stronger the attachment of the beverage dispenser to the wall extensions. The wall extensions and beverage dispenser may be configured to incorporate other connection mechanisms to attach the wall extensions and the beverage dispenser.

Figure 31:
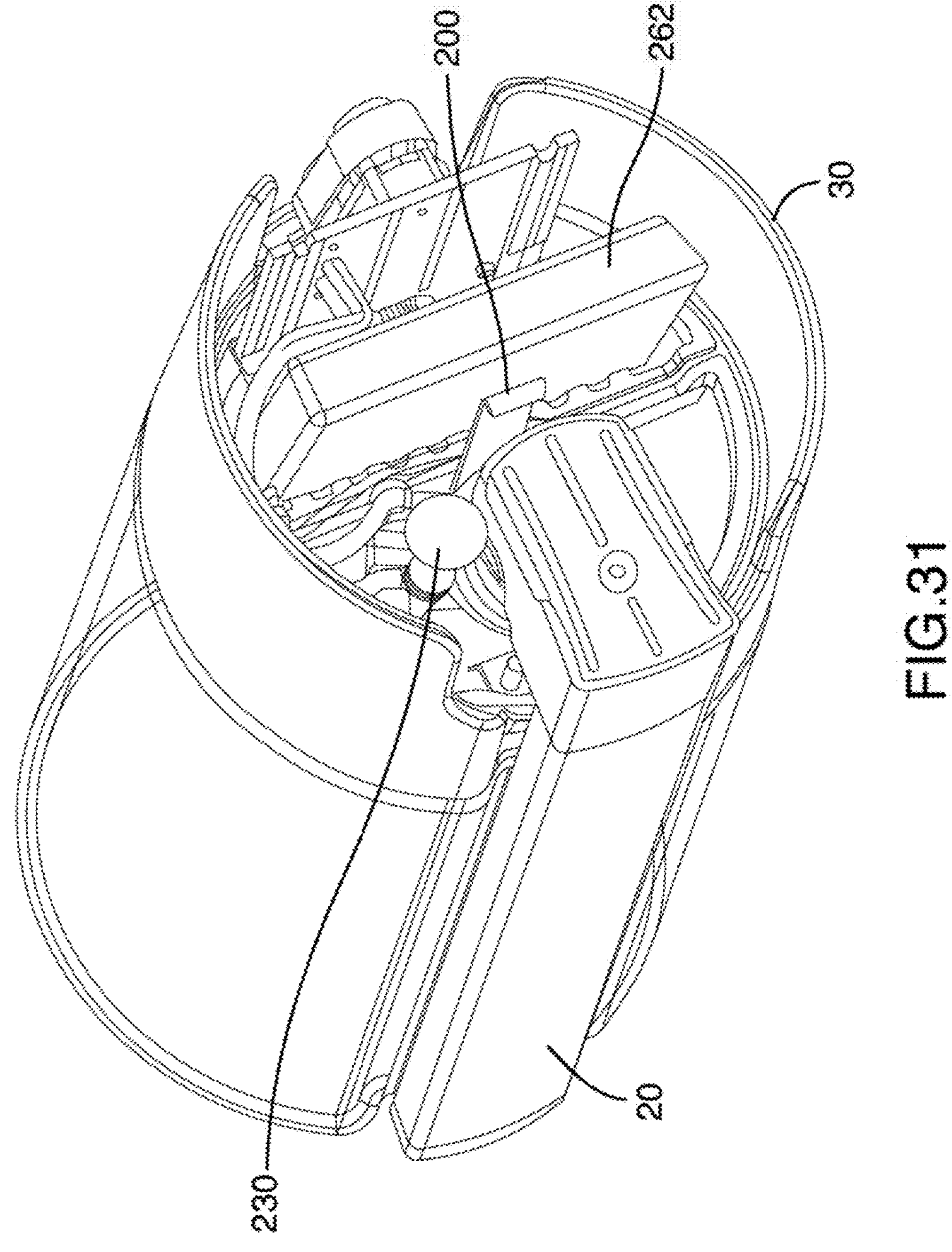
FIG. 31 is a base sectional view of a beverage and vapor dispenser, of an embodiment of the present invention.
Figures 32A, 32B, 32C, 32D:
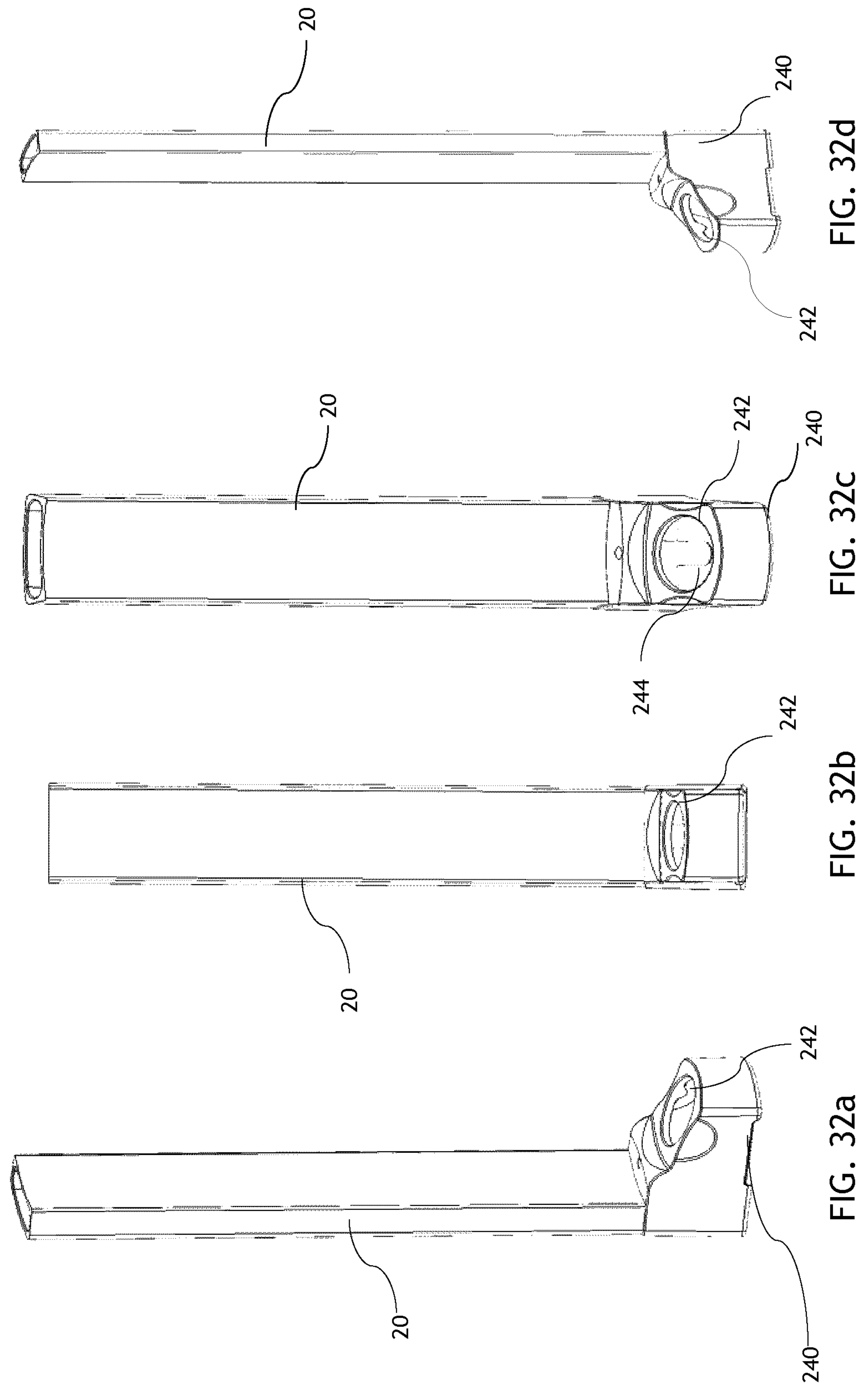
FIG. 32*a* is a side perspective view of a conduit section, of an embodiment of the present invention.
FIG. 32*b* is a back sectional view of a conduit section, of an embodiment of the present invention.
FIG. 32*c* is a front perspective view of a conduit section, of an embodiment of the present invention.
FIG. 32*d* is a side perspective view of a conduit section, of an embodiment of the present invention.

The wall extensions 1038 fit over a portion of the housing of the base unit 30. The base unit elements 32 fit within the base unit (for example, the base unit elements, including the battery 262, are shown fit within the base unit in FIG. 31) and are covered by the upper portion of the housing of the base unit. The housing of the base unit may incorporate a slot, hole or other mechanism whereby the herb stirrer 230 can be stored when it is not in use.

The housing of the base unit may further incorporate a conduit hole 236 wherein a portion of the conduit section 20 may be inserted to incorporate the conduit section with the base unit. The portion of the conduit section that is inserted into the conduit hole may incorporate a chamber tray 1042, positioned such that when the portion of the conduit section is inserted into the conduit hole, the chamber tray is enclosed within the housing of the base unit. The end of the conduit section that is not inserted within the housing of the base unit may have a tip connected thereto. The tip may be configured such that a portion of the tip fits within the conduit section and a portion of the tip extends outside of the conduit section when the tip is connected or otherwise attached to the conduit section.

The portion of the conduit section that fits into the conduit hole, and is thereby inserted within the housing of the base unit, may have a variety of configurations. An example of a configuration for this type of conduit section is shown in FIGS. 32*a*, 32*b*, 32*c* and 32*d*. The herb chamber 240 may be connected to and incorporated into the conduit section 20. The herb chamber may incorporate a chamber tray holder 242 configured to be operable to hold the chamber tray in place within the herb chamber. The herb chamber may further incorporate an accessible cooling chamber 244 positioned between the portion of the conduit section that is not inserted within the housing of the base unit and the herb chamber. The cooling chamber may be configured to achieve cooling of the vapor that passes from the chamber tray into the conduit section. In some embodiments of the present invention, dry ice may be inserted into the cooling chamber or other areas within the herb chamber. The dry ice may act to augment the effect of the cooling chamber to cool the vapor and to otherwise interact with the vapor as discussed herein. It may further be possible to insert dry ice into the chamber tray, as discussed herein.

Figure 33:
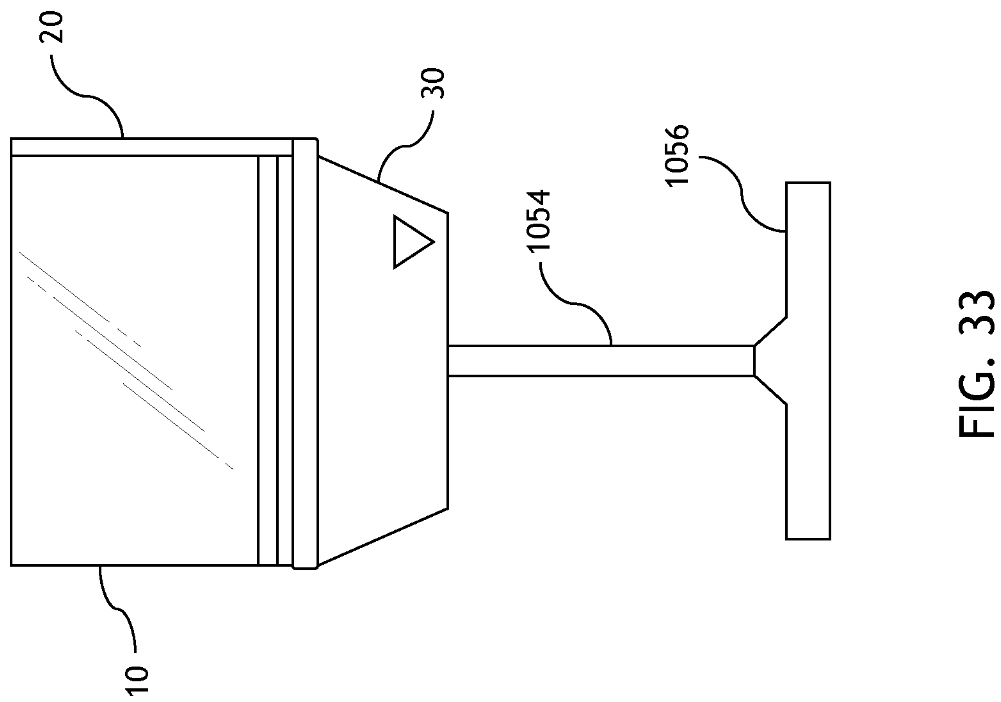
FIG. 33 is a side view of the beverage and vapor dispenser, of an embodiment of the present invention.

A skilled reader will recognize that there are many possible embodiments of the present invention, as discussed herein. For example, in an embodiment of the present invention, as shown in FIG. 33, the beverage dispenser may be a wine glass, and the base unit may be positioned between the bowl of the wine glass and the stem 1054 and base 1056 of the wine glass.

Figure 35:
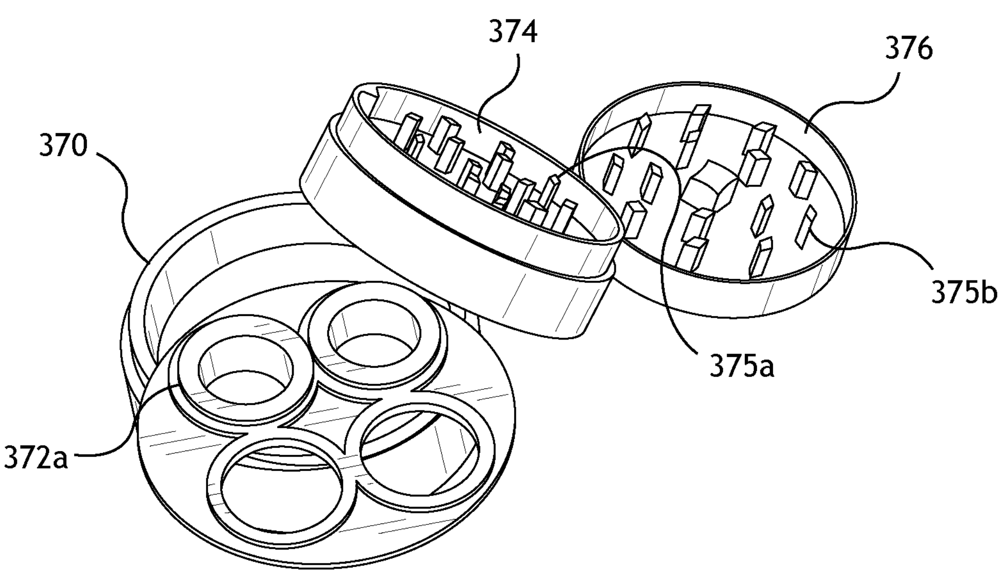
FIG. 35 is an exploded view of a multiple herb dispenser, of an embodiment of the present invention.
Figure 36:
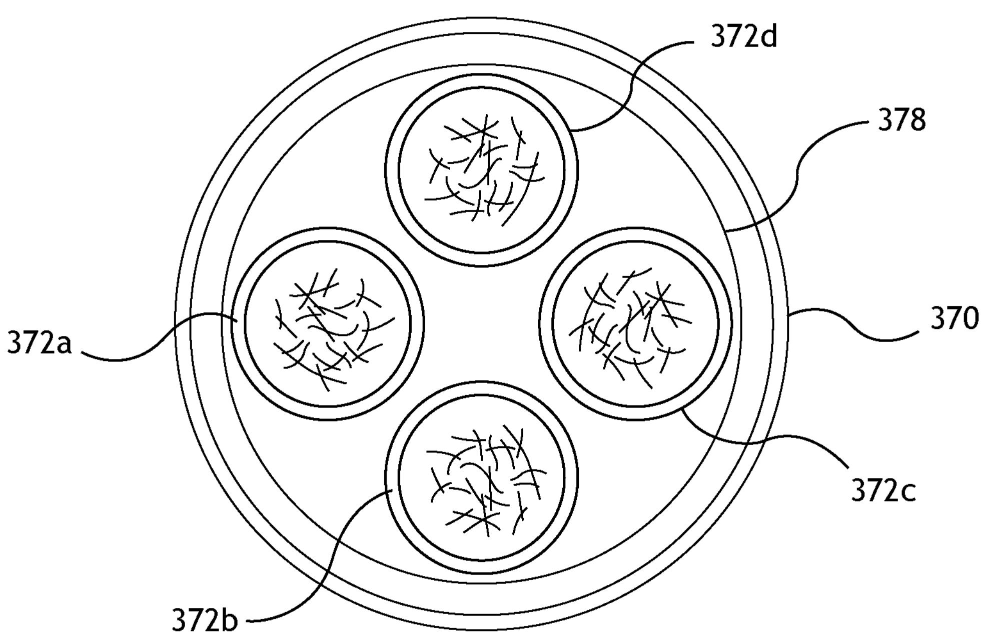
FIG. 36 is a top view of a multiple herb dispenser, of an embodiment of the present invention.

In another embodiment of the present invention a cartridge wheel tray 370 may be utilized, as shown in FIGS. 35 and 36. The cartridge wheel tray may be configured to hold multiple herb cartridges 372*a*, 372*b*, 372*c*, 372*d*. The cartridges may be loaded with granulated herbs. Lids for the cartridge wheel 374, 376 may incorporate one or more posts 375*a*, 375*b* that may be utilized to grind the herb within the cartridges, in a manner similar to that described as the grinding function of the herb stirrer. Different lids may be configured to incorporate posts having different sizes, lengths and/or widths that will produce different types of grinds (e.g., finer or coarser) when applied to the herbs in the cartridges. The benefit of the grind created by the lids is that a consistent and even grind of the herbs may be produced. As discussed herein, the grind of herbs can produce benefits for vaporization. The lids having posts for grinding may be applied only to grind the herbs, and a lid without any such posts or other grinding elements may be applied when the present invention is assembled.

The herb cartridges may each contain an herb, which may be the same herb or different herbs. Depending on the position of the cartridge wheel tray in relation to the heating chamber, the herb in one or more cartridges may be heated so as to create vapor therefrom. If multiple cartridges are heated to produce vapor, the vapor produced may be a blend of herbs achieved through a method that does not require the combination of multiple herbs within a single chamber tray.

The cartridges may function in a similar manner to chamber trays, and may be washable and reuseable, as described herein for chamber trays. Cartridges may also be disposable. In some embodiments of the present invention, the cartridges may be provided as pre-filled, whereby the content and potency thereof may be identified to a user, and such content may be in accordance with a prescription, potency, or other requirement relating to the vapor from the herb to be delivered to the user.

The cartridge wheel tray 370 may incorporate an inner wheel 378 whereby the inner wheel may be rotated independently from the cartridge wheel tray. This function may assist with grinding of herbs. The inner wheel may be rotated in a forward and backward motion, to cause interaction between the herb and the posts in the lids that will result in the herb being ground. The position of the cartridge wheel may further be utilized to cause chamber trays within the cartridge wheel to be positioned in proximity to matching openings in the lids above. This allows the ground herbs to be deposited within the chamber tray for retrieval and use by the user.

Figure 37:
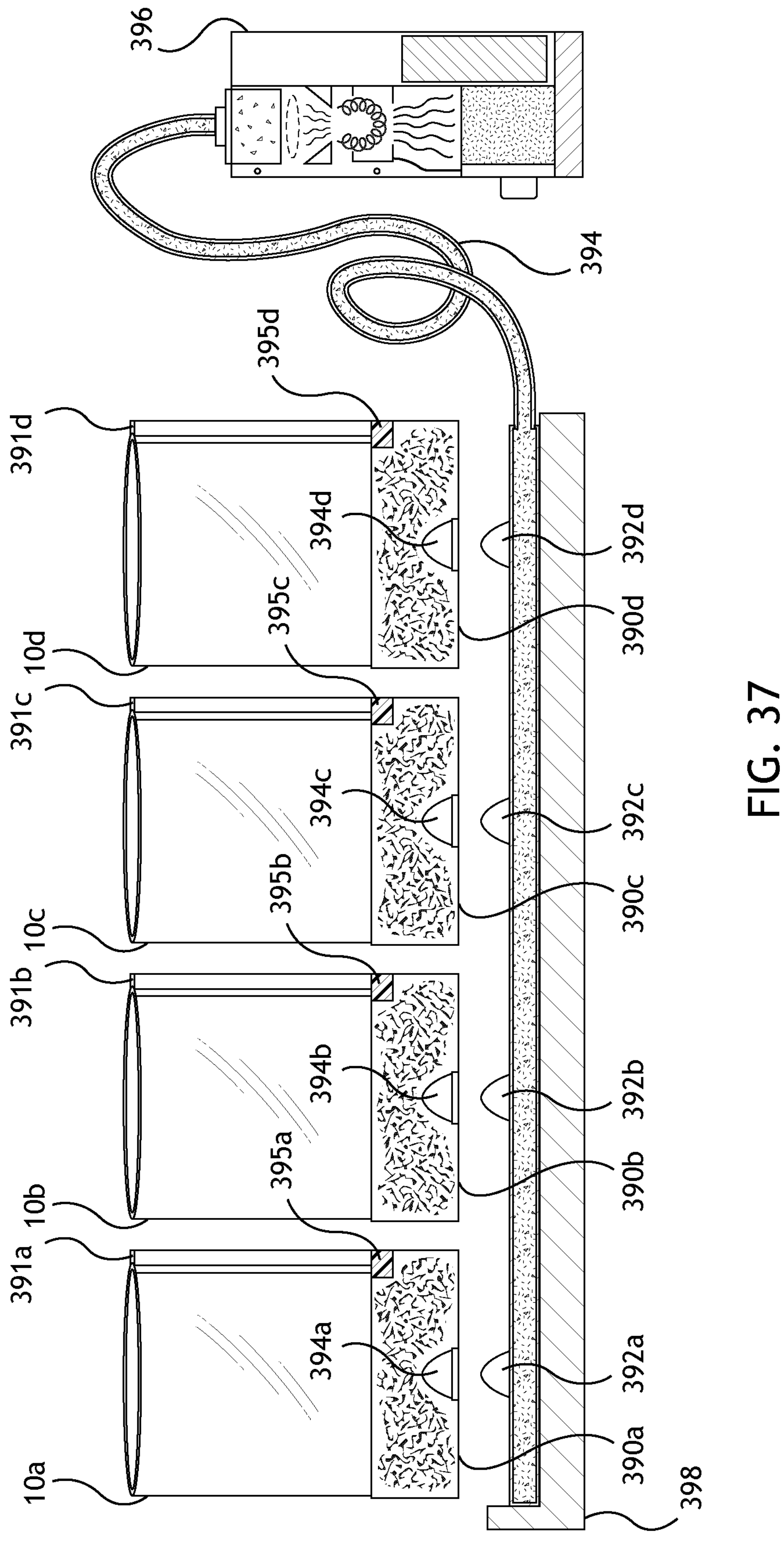
FIG. 37 is a vaporizer unit and multiple beverage dispensers, of an embodiment of the present invention.

In another embodiment of the present invention, as shown in FIG. 37, multiple vapor and beverage dispensers 391*a*, 391*b*, 391*c*, 391*d*, are positionable upon a vapor tray 398. The vapor and beverage dispensers can be formed of a variety of materials, including glass, ceramic, plastic, or other materials. Each vapor and beverage dispenser is attached to, or incorporates, a vapor holder section 390*a*, 390*b*, 390*c*, 390*d*. The vapor holder has a hollow interior wherein vapor can be stored. Each vapor and beverage dispenser further incorporates a vapor conduit 391*a*, 391*b*, 391*c*, 391*d* that is attached to a vapor outlet in the vapor holder attached to such vapor and beverage dispenser.

The vapor outlet is positioned at, or near where the vapor conduit is attached to the vapor holder, and comprises a hole in the vapor that permits the flow of vapor from the vapor holder to the conduit section. When vapor is captured within the vapor holder, the vapor will flow through the vapor outlet and into the vapor conduit. In some embodiments of the present invention the vapor outlet may be connected to an outlet tube that connects to the vapor conduit, in a similar manner as described herein for the connection between the base unit outlet and a conduit section.

Each vapor holder is mountable upon a vapor dispenser 392*a*, 392*b*, 392*c*, 392*d*. When the vapor holder is mounted upon the vapor dispenser the vapor dispenser opens both an outlet in the vapor dispenser, as well as an inlet 394*a*, 394*b*, 394*c*, 394*d* in the base of the vapor holder. When the vapor dispenser outlet and the vapor holder inlet are opened vapor can flow from the vapor tray through the vapor dispenser and into the vapor holder. When a vapor holder is lifted from the vapor dispenser the vapor dispenser outlet and the vapor holder inlet are closed. When the vapor dispenser outlet is closed vapor cannot flow out from the vapor tray through the vapor dispenser outlet. When the vapor holder inlet is closed, vapor cannot flow out from the vapor holder inlet.

A flexible conduit 394 is attached at its one end to the vapor tray 398 and at its other end to a vaporizer base unit 396. The vaporizer base unit incorporates the elements of the base unit discussed herein, and is operable to generate vapor from herb content. The configuration of the elements within the vaporizer base unit will be arranged to generate vapor from herb content in a chamber tray of an herb chamber that is positioned in close proximity to a heating chamber that incorporates heating coils. The heating chamber may be above or below the herb chamber in the vaporizer base unit. There may further be an air inlet in the vaporizer base unit whereby convection heating is applied to generate vapor from the herb content in the chamber tray.

Dry ice may be consistently, or intermittently, positioned within the vaporizer base unit near the connection of the flexible conduit to the vaporizer base unit, whereby the vapor is affected as discussed herein, so that the vapor is cooled and the flavor of the vapor is enhanced.

When vapor is generated by the vapor base unit, the vapor will flow into and along the flexible conduit, and from the flexible conduit into the vapor tray. When a vapor and beverage dispenser is positioned upon a vapor dispenser, vapor in the vapor tray will flow into the vapor holder. The path of the vapor flow will pass from the vapor tray through the vapor dispenser outlet, into the vapor holder inlet, and thereby into the vapor holder. A user may raise the vapor and beverage dispenser from the vapor tray. When a vapor and beverage dispenser is not in contact with the vapor dispenser, the vapor dispenser, and the vapor dispenser outlet, will be in a closed position whereby no vapor can flow from the vapor tray through the vapor dispenser. For example, the vapor dispenser may have a pressure seal incorporated therein, whereby the vapor dispenser, and the outlet of the vapor dispenser, is sealed when there is no vapor and beverage dispenser positioned thereon, and the seal is moved to an open position when a vapor and beverage dispenser is positioned upon the vapor dispenser.

The inlet for the vapor holder may have a similar mechanism to the vapor dispenser outlet, such as a pressure seal, to open and close the vapor holder inlet.

Such an embodiment of the present invention may incorporate mechanisms to direct the flow of the vapor, such as elements that affect the pressure within the vapor tray, fans or other elements that can affect the flow of vapor within the vapor tray, depending on the capacity and configuration of the vapor tray.

A plug, flex pressure seal, or other barrier may be positioned over the vapor outlet of the vapor holder. The plug, seal or other barrier may be moved to an open or closed position by the user. For example, a button on the external wall of the vapor holder may be attached to a mechanism whereby the plug, seal or other barrier may be moved, such that the outlet will be altered between an open and closed state. When the plug, seal or other barrier is removed or opened vapor will travel from the vapor holder into the vapor conduit. A user may inhale the vapor from the vapor conduit, such as through the nose or through the mouth, in the manner discussed herein. A user may control the amount of vapor that is delivered to a user via the vapor conduit through use of the dispensing button 395*a*, 395*b*, 395*c*, 395*d*.

The dispensing button may be operable to move the vapor outlet of the vapor holder between an open and closed state. For example, a user may open the vapor outlet and allow a portion of the vapor to flow into the vapor conduit and then use the button to close the vapor outlet. The user may again use the button to open the vapor outlet to cause more of the vapor to be delivered from the vapor holder to the vapor conduit, and thereby to the user, at a later point in time. In some embodiments of the present invention the vapor outlet may remain open while the dispensing button is pressed by a user, and the vapor outlet will be closed when the dispensing button is not pressed by a user. Other mechanisms for moving the vapor outlet between an open and closed position by use of the dispensing button may be incorporated in embodiments of the present invention.

The embodiment of the present invention shown in FIG. 37 is operable to deliver vapor to multiple users simultaneously in individual vapor and beverage dispensers. Each of the beverage dispensers may be utilized to hold liquid. The elements of the vaporizer base unit 396 of this embodiment of the present invention may be configured to generate sufficient vapor for multiple users, and therefore the heating chamber, chamber tray and other elements of the vaporizer base unit may be operable to generate a larger capacity of vapor than the elements of the base unit of embodiments of the present invention that are operable for use by a single user. For example, the chamber tray or wheel tray of the vaporizer base unit 396 may be of a sufficient size the hold enough herb to generate vapor for multiple users, which may be a greater quantity of herb than utilized with embodiments of the present invention for use by an individual user. The heating chamber of the vaporizer base unit 396 may also be operable to heat the larger quantity of herb. Other elements of the present invention may also be altered in size or capacity as required to be operable to generate vapor for multiple users simultaneously.

The vaporizer base unit may be battery powered, powered by a connection to an electrical outlet, or powered by a combination of battery and electricity. The battery or other power source may be connected to elements of the vaporizer base unit that require power, such as the heating chamber, any lights or screens, and/or other elements.

Although four vapor and beverage dispensers are shown in FIG. 37, this is merely an example, and this embodiment of the present invention may incorporate more or fewer than 4 vapor and beverage dispensers.

Figure 40:
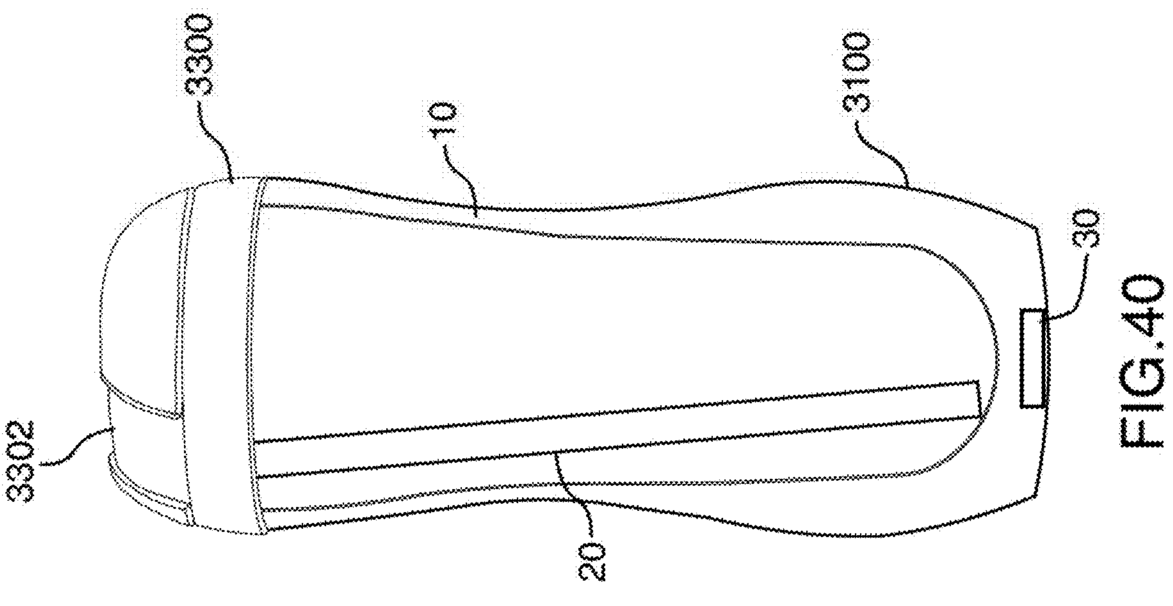
FIG. 40 is a front view of the beverage and vapor dispenser incorporating a transparent vapor section, of an embodiment of the present invention.
Figure 39:
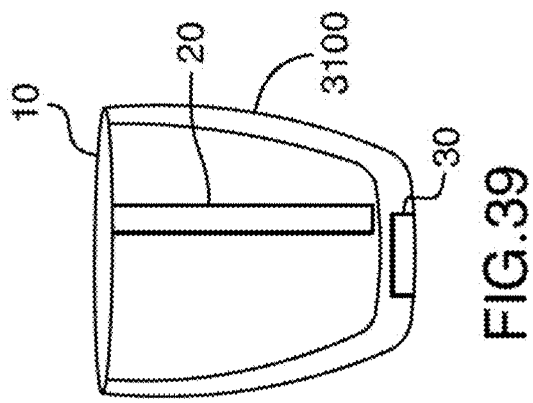
FIG. 39 is a front view of the beverage and vapor dispenser incorporating a transparent vapor section, of an embodiment of the present invention.
Figure 38:
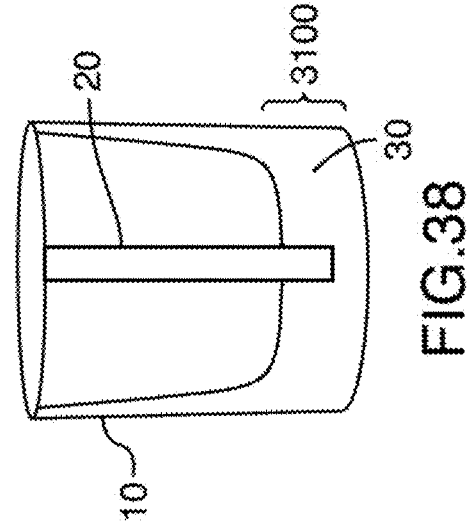
FIG. 38 is a front view of the beverage and vapor dispenser incorporating a transparent vapor section, of an embodiment of the present invention.

In still other embodiments of the present invention, the base unit can be incorporated within a beverage dispenser shaped to incorporate a viewable portion 3100, as shown in FIGS. 38, 39, 40. In such embodiments of the present invention, the base unit 30 will incorporate the elements discussed herein that operate to generate vapor from herb chamber content. The vapor will be disbursed from an outlet in the base unit into the viewable portion. A conduit section is incorporated within the beverage dispenser and extends into an outlet in the viewable portion, whereby vapor travels from the viewable portion to the conduit section, and thereby to a user. The beverage dispenser in such an embodiment of the present invention can be of various types, such as a glass, as shown in FIG. 38, a cup, as shown in FIG. 39, or a bottle with a plastic cap 330 and a flip lid 3302, as shown in FIG. 40. The viewable portion incorporates a door whereby the base unit can be removed from the viewable portion, so that the base unit and elements therein can be cleaned, fixed, or have herb content removed therefrom or placed therein.

It will be appreciated by those skilled in the art that other variations of the embodiments described herein may also be practiced without departing from the scope of the invention. Other modifications are therefore possible.

The invention claimed is:

1. A beverage and vapor dispenser comprising:

a. a base unit incorporating: a herb chamber operable to contain one or more herbs; a heating chamber operable to produce heat and generate vapor from a herb; and a vapor outlet, whereby the vapor can flow out of the base unit, the base unit incorporating a heat activation button operable to produce heat from the heating chamber;

b. a beverage dispenser removably connected to the base unit, the beverage dispenser being operable to contain and dispense liquid, and the beverage dispenser being positionable upon the base unit whereby the beverage dispenser rests upon the base unit and when so positioned the base unit bears and supports the beverage dispenser's weight and forms a base of the beverage dispenser and the base unit is positioned below a bottom surface of the beverage dispenser whereby an upper surface of the base unit is in direct contact with the bottom surface of the beverage dispenser;

c. a conduit section having a hollow interior, the conduit section being removably connectable to the vapor outlet of the base unit and when so connected the vapor can flow from the base unit through the conduit section to a user; and d. a conduit section indentation in a wall of the beverage dispenser, wherein the conduit section is positioned virtually parallel to the wall of the beverage dispenser.

2. The beverage and vapor dispenser of claim 1, further comprising the heating chamber incorporating heating coils powered by a power source.

3. The beverage and vapor dispenser of claim 1, further comprising the herb chamber having dry ice therein.

4. The beverage and vapor dispenser of claim 1, further comprising a removable chamber tray incorporated in the herb chamber, wherein the herb is placed and from which herb residue is removed.

5. The beverage and vapor dispenser of claim 1, further comprising a heat indicator in the base unit, said heat indicator being one of the following: one or more lights; or a screen operable to display information.

6. The beverage and vapor dispenser of claim 1, further comprising a heat setting indicator in the base unit said heat setting indicator being one of the following: one or more lights; or a screen operable to display information.

7. The beverage and vapor dispenser of claim 1, further comprising one or more of the following: a heat increase button; a heat decrease button; a heat setting increase button; and a heat setting decrease button.

8. The beverage and vapor dispenser of claim 1, further comprising the base unit, conduit section and beverage dispenser being wholly detachable, whereby base unit, conduit section and beverage dispenser can be cleaned or repaired individually, or replaced before the beverage and vapor dispenser is reassembled.

9. The beverage and vapor dispenser of claim 1, further comprising a tip removably attachable to an end of the conduit section that is not attached to the vapor outlet, said tip having a hollow interior.

10. The beverage and vapor dispenser of claim 9, further comprising one or more holes in the tip, whereby vapor can flow from the tip when the tip is connected to the conduit section.

11. The beverage and vapor dispenser of claim 1, further comprising said heating chamber being positioned above the herb chamber.

12. The beverage and vapor dispenser of claim 1, further comprising an extension wall section attachable to or incorporated in the beverage dispenser, whereby the beverage dispenser is attachable to the base unit.

13. A beverage and vapor dispenser comprising:

a. a base unit incorporating: a herb chamber operable to contain one or more herbs; a heating chamber operable to produce heat and generate vapor from a herb; and a vapor outlet, whereby the vapor can flow out of the base unit;

b. a beverage dispenser removably connected to the base unit, said beverage dispenser being operable to contain and dispense liquid; and c. a conduit section having a hollow interior, said conduit section being removably connectable to the vapor outlet of the base unit and when so connected the vapor can flow from the base unit through the conduit section to a user, and d. a conduit section indentation in a wall of the beverage dispenser, wherein the conduit section is positioned virtually parallel to the wall of the beverage dispenser.

14. The beverage and vapor dispenser of claim 1, further comprising the beverage dispenser incorporating a vapor viewable portion operable to contain and display vapor.

15. The beverage and vapor dispenser of claim 1, further comprising the herb chamber incorporating multiple herb chambers or multiple herb cartridges.

16. The beverage and vapor dispenser of claim 1 operable to generate the vapor by convection heating, said beverage and vapor dispenser comprising:

a. the conduit section having the heating chamber incorporated therein; and b. the base unit incorporating an air inlet whereby air flows into the base unit, the conduit section being attachable to the base unit such that the heating chamber of the conduit section is positioned within the base unit in proximity to the heating chamber that is above the herb chamber, the heating chamber and air flow into the air inlet generating convection heating.

17. A method of using the beverage and vapor dispenser of claim 1, in accordance with the following steps:

a. placing one or more herbs within a herb chamber in a base unit of the beverage and vapor dispenser;

b. pouring liquid into the beverage dispenser of the beverage and vapor dispenser;

c. activating a heating chamber in the base unit to produce heat, whereby vapor is generated from the herb;

d. a user inhaling vapor flowing from the base unit through a conduit section; and e. dispensing the liquid from the beverage dispenser to the user.

18. The method of claim 17, comprising the further step of the user inhaling vapor from the conduit section by mouth, by sucking on the conduit section.

19. A beverage and vapor dispenser comprising:

a. two or more beverage dispensers each incorporating a hollow vapor holding section having a vapor inlet and a vapor outlet therein, and a vapor conduit section being hollow and removably connectable to the vapor outlet;

b. a hollow vapor tray incorporating a vapor tray inlet, and two or more vapor dispensers having a door therein that is openable when the vapor inlet of a beverage dispenser is positioned upon the vapor dispenser;

c. a vaporizer base unit incorporating a heating chamber operable to produce heat and generate vapor from a herb within a herb chamber, and a vaporizer outlet; and d. a hollow connector having a first end connected to the vapor tray inlet and a second end connected to the vaporizer outlet;

whereby the vapor flows: from the vaporizer base unit through the connector into the vapor tray; from the vapor tray through a vapor dispenser into the vapor holding section of a beverage dispenser placed thereupon; and from the vapor holding section through the vapor conduit section to a user.

* * * * *